(12) United States Patent
Zhang et al.

(10) Patent No.: US 9,297,801 B2
(45) Date of Patent: Mar. 29, 2016

(54) GOLD NANOPARTICLE AGGREGATES AND THEIR APPLICATIONS

(75) Inventors: Jin Zhang, Santa Cruz, CA (US); Adam Schwartzberg, Santa Cruz, CA (US); Thaddeus Norman, San Jose, CA (US); Tammy Y. Oshiro, Santa Cruz, CA (US); Christian D. Grant, San Jose, CA (US); Rebecca Sutphen, Tampa, FL (US); Leo Seballos, Santa Cruz, CA (US); Yi Zhang, Santa Cruz, CA (US); Claire Gu, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 870 days.

(21) Appl. No.: 13/199,563

(22) Filed: Sep. 3, 2011

(65) Prior Publication Data

US 2012/0142119 A1    Jun. 7, 2012

Related U.S. Application Data

(63) Continuation of application No. 11/396,098, filed on Mar. 30, 2006, now abandoned.

(60) Provisional application No. 60/667,151, filed on Mar. 30, 2005, provisional application No. 60/711,808, filed on Aug. 26, 2005.

(51) Int. Cl.
  *G01N 33/553* (2006.01)
  *G01N 33/543* (2006.01)
  *G01N 33/58* (2006.01)

(52) U.S. Cl.
  CPC ........ *G01N 33/553* (2013.01); *G01N 33/54313* (2013.01); *G01N 33/585* (2013.01)

(58) Field of Classification Search
  CPC .. G01J 3/0218; G01J 1/0433; G01N 15/0205; G01N 2015/1493; G01N 21/65
  USPC .................................................. 436/525, 518
  See application file for complete search history.

(56) References Cited

U.S. PATENT DOCUMENTS 6,579,721 B1 *  6/2003  Natan et al. .................. 436/164

OTHER PUBLICATIONS

Norman et al. "Longitudinal Plasma Resonance Shifts in Gold Nanoparticle Aggregates", Proceedings of SPIE vol. 4807, (2002).*

* cited by examiner

*Primary Examiner* — Bao Thuy L Nguyen
*Assistant Examiner* — Pensee Do
(74) *Attorney, Agent, or Firm* — Matthew Kaser; Adam Warvick Bell

(57) ABSTRACT

The invention is drawn to a method of using nanoparticle aggregates to form sensors and optical filters. Properly sized (60 and 200 nm) nanoparticle aggregates with cores having a sulfur-oxygen molecular species and a shell with a surface in contact with the core are obtained. Those nanoparticle aggregates have a first resonance profile to wavelengths between 350 nm and 1075 nm. A modified resonance profile for those nanoparticle aggregates is determined. The nanoparticle aggregates are then selectively sized by irradiating them with electromagnetic energy at sufficient intensity and spectral content to modify the first resonance profile towards the modified resonance profile. The resulting nanoparticle aggregates can be used as sensors or optical filters at a selected wavelength.

16 Claims, 11 Drawing Sheets

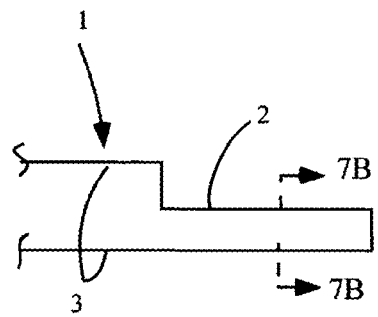
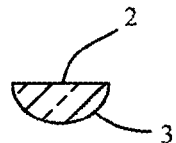
Fig. 7A                    Fig. 7B
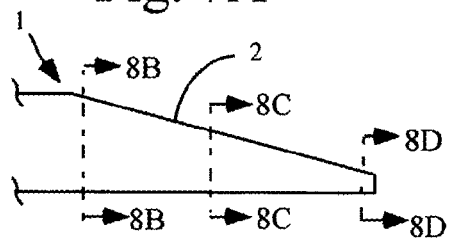
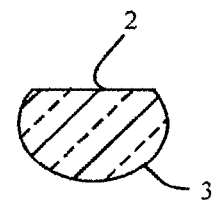
Fig. 8A                    Fig. 8B
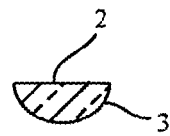
Fig. 8C                    Fig. 8D
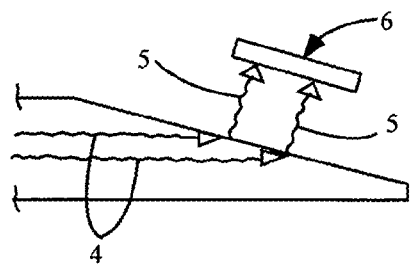
Fig. 9

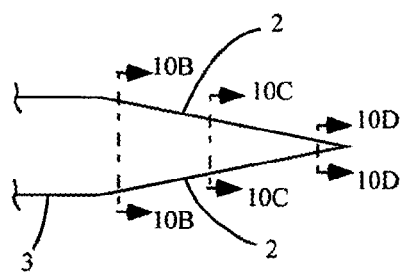
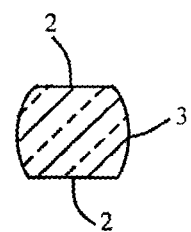
Fig. 10A  Fig. 10B
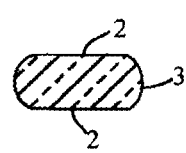
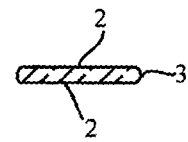
Fig. 10C  Fig. 10D
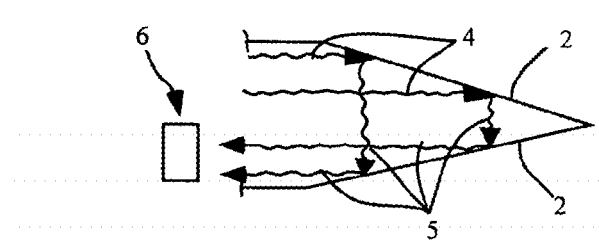
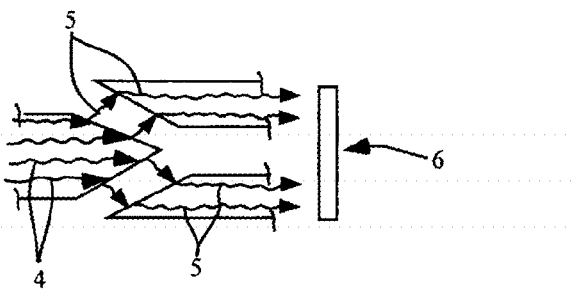
Fig. 11  Fig. 12
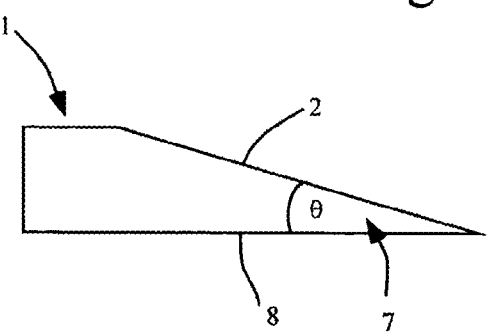
Fig. 13

GOLD NANOPARTICLE AGGREGATES AND THEIR APPLICATIONS

RELATIONSHIP TO OTHER APPLICATIONS

This is a continuation of prior application Ser. No. 11/396,098, filed Mar. 30, 2006. This application to the extent allowed by law, claims priority to and the benefit of the following applications: U.S. Provisional Patent Application Ser. No. 60/667,151 entitled "Novel Gold Nanoparticle Aggregates and Their Applications", filed Mar. 30, 2005, and U.S. Provisional Patent Application Ser. No. 60/711,808 entitled "Novel Gold Nanoparticle Aggregates and Their Applications", filed Aug. 26, 2005, which are herein incorporated by reference in their entirety for all purposes.

FIELD OF THE INVENTION

The present invention relates to particles comprising a metallic core and sulfur species on their surface with useful properties. The invention further relates to methods of using the particles for detecting chemical and biological analytes, and in use in optical communications.

BACKGROUND OF THE INVENTION

During the 1980s Raman Scattering in fibers was demonstrated by Lin, Stolen, and other co-workers of AT&T Bell Laboratories in Holmdel, N.J. using Raman lasers operating between 0.3 to 2.0 µm. In the early years of the Raman fiber before extensive work had begun, no one perceived that a Raman fiber could be pumped by a practical semiconductor laser-based source or that an efficient CW-pumped Raman Fiber Laser was possible. However, with the development of Cladding-pumped Fiber Lasers and Fiber Bragg Gratings, diode-laser-based CW Raman Fiber Lasers have been made efficient, emitting at various wavelengths throughout the infrared spectrum a reality. (See van Gisbergen et al. (1996) Chem. Phys. Lett. 259: 599-604.)

Raman spectroscopy is a powerful optical technique for detecting and analyzing molecules. Its principle is based on detecting light scattered off a molecule that is shifted in energy with respect to the incident light. The shift, called Raman shift, is characteristic of individual molecules, reflecting their vibrational frequencies that are like fingerprints of molecules. As a result, the key advantage of Raman spectroscopy is its molecular specificity while its main limitation is the small signal due to low quantum yield of Raman scattering. One way to enhance the Raman signal is to tune the excitation wavelength to be on resonance with an electronic transition, so called resonance Raman scattering. This can usually produce an enhancement on the order of $10^2$-$10^3$.

Another technique to enhance Raman scattering is surface enhancement by roughened metal surfaces, notably silver and gold, that provides an enhancement factor on the order of $10^6$-$10^8$. This is termed surface enhanced Raman spectroscopy (SERS). Similar or somewhat larger enhancement factors (~$10^8$-$10^{10}$) have been observed for metal, mostly silver or gold, nanoparticles.

In the last few years, it has been shown that an even larger enhancement (~$10^{10}$-$10^{15}$) is possible for aggregates of metal nanoparticles (MNPs), silver and gold. The largest enhancement factor of $10^{14}$-$10^{15}$ has been reported for rhodamine 6G (R6G) on single silver nanoparticle aggregates. This huge enhancement is thought to be mainly due to significant enhancement of the local electromagnetic field of the nanoparticle aggregate that strongly absorbs the incident excitation light for the Raman scattering process. With such large enhancement, many important molecules that are difficult to detect with Raman normally can now be easily detected. This opens many interesting and new opportunities for detecting and analyzing molecules using SERS with extremely high sensitivity and molecular specificity.

SERS can also be developed into a molecular imaging technique for biomedical and other applications. Existing Raman imaging equipment should be usable for SERS imaging. SERS will provide a much-enhanced signal and thereby significantly shortened data acquisition time, making the technique practically useful for medical or other commercial and industrial applications including chip inspection or chemical monitoring. SERS is also useful for detecting other cancer biomarkers that can interact or bind to the MNP surface. For example, Sutphen et al. have recently shown that lysophospholipids (LPL) are potential biomarkers of ovarian cancer (Sutphen et al. (2004) Cancer Epidemiol. Biomarker Prev. 13: 1185-1191).

For many practical applications, for example SERS and optical filters, it is highly desirable to narrow the distribution of size/shape of nanoparticle aggregates. For SERS in particular, the incident light has to be on resonance with the substrate absorption. Only those nanoparticle aggregates that have resonance absorption of the incident light are expected to be SERS active. It is thus extremely beneficial to have a narrow size/shape distribution and thereby narrow optical absorption.

Fluorescent nanoparticles (quantum dots (QDs) such as semiconductor quantum dots, SQDs) have been used recently as fluorescent biological markers and have been found to be extremely effective. They offer advantages including higher stability, stronger fluorescence, tunability of color, and possibility of optical encoding based on different sized or colored SQDs.

A method of synthesis for gold nanoparticle aggregates (GNAs) has been described in the prior art (see Norman et al. (2002) J. Phys. Chem. B, 106: 7005-7012). Norman used $Na_2S$ and $HAuCl_4$ (chloroauric acid). Norman suggested that the product of the reaction is elemental sulfur, elemental gold, free protons, and free chlorine ions. This contrasts with the alternative dogma that the aggregates comprise an $Au_2S$ core enveloped by an Au shell. Therefore Norman concluded that the reaction produces aggregates of gold nanoparticles having amorphous sulfur on their surface.

Metal nanoparticles have been recognized for their unique optical properties that could be exploited in optoelectronic devices. Nanoparticle systems composed of gold, for example, have distinct optical properties that make them amenable to study by Raman scattering. The Raman spectrum of the adsorbed species is significantly enhanced by 10 to 15 orders of magnitude when the metal nanoparticles have aggregated, leading to enhanced electromagnetic field effects near the surface that increases the Raman scattering intensity. The greater sensitivity found in the surface enhanced Raman spectroscopy (SERS) of metal nanoparticle aggregates facilitates the detection and analysis of a whole host of molecules that were previously difficult to study.

Wang et al. disclose a method of using SQDs (dye-conjugated CdTe nanoparticles, CT-NPs) to detect interactive binding between Ag-CT-NPs and Ab-CT-NPs (Wang et al. (2002) NanoLett. 2: 817-822). The interactions were determined by differential quenching or enhancement fluorescence activity of two different sized SQDs (red or green) measured during the analysis.

The chemical methods used historically for the production of gold nanoparticle aggregates (GNAs) results in a wide distribution of aggregate size. This distribution leads to a broadened absorption spectrum. Accordingly, researchers have attempted to narrow the lineshape of the spectral peak due to the aggregates by homogenizing the size of the GNAs after they have been produced. By eliminating certain ranges of aggregate size, absorption spectrum peaks should narrow appreciably and concomitantly increase in intensity, resulting in more sensitive detection. Previous attempts to select for a narrow size range of aggregates have employed mechanical techniques such as passing a solution of aggregates through a filter. For example, Emory & Nie have employed size-selective fractionation using membrane filters to select for optically active silver nanoparticles (Emory and Nie, (1997) J. Phys. Chem. B, 102: 493-497).

The use of SERS for analyte detection of biomolecules has been previously studied. U.S. Pat. No. 6,699,724 to West et al. describes a chemical sensing device and method (nanoshell-modified ELISA technique) based on the enzyme-linked immunoadsorbant assay (ELISA). The chemical sensing device can comprise a core comprising gold sulfide and a surface capable of inducing surface enhanced Raman scattering (SERS). In much of the patent disclosure, the nanoparticle is disclosed as having a silica core and a gold shell. The patent discloses that an enhancement of 600,000-fold ($6 \times 10^5$) in the Raman signal using conjugated mercaptoaniline was observed.

In the nanoshell-modified ELISA technique, antibodies are directly bound to the metal nanoshells. Raman spectra are taken of the antibody-nanoshell conjugates before and after the addition of a sample containing a possible antigen, and binding of antigen to antibody is expected to cause a detectable shift in the spectra.

The conjugation of quantum dots to antibodies used for ultrasensitive nonisotopic detection for use in biological assays has also been studied. U.S. Pat. No. 6,468,808 B1 to Nie et al. disclosed an antibody is conjugated to a water-soluble quantum dot. The binding of the quantum dot-antibody conjugate to a targeted protein will result in agglutination, which can be detected using an epi-fluorescence microscope. In addition, Nie et al. described a system in which a quantum dot is attached to one end of an oligonucleotide and a quenching moiety is attached to the other. The preferred quenching moiety in the Nie patent is a nonfluorescent organic chromophore such as 4-[4'-dimethylaminophenylazo]benzoic acid (DABCYL).

Raman amplifiers are also expected to be used globally as a key device in next-generation optical communications, for example, in wavelength-division-multiplexing (WDM) transmission systems. Raman scattering occurs when an atom absorbs a photon and another photon of a different energy is released. The energy difference excites the atom and causes it to release a photon with low energy; therefore, more light energy is transferred to the photons in the light path.

FIG. 6 shown how the Raman amplifier operates. The Raman amplification process begins as a seed beam (incoming light) passes through the optical fiber. While it is traveling, a stronger pump beam is released from another light source and is deflected using a refractive material, such as a mirror. The pump beam and seed beam then come in contact with each other and the seed beam depletes the energy of the pump beam; therefore the intensity of the light increases and the signal is amplified. Now the signal is capable of traveling long distances, for example, more than 70 km, without losing a signal. (See, for example, U.S. Pat. No. 6,292,288; Vinson and Webb (2001) Light Amplification: The Future Of Optical Communications, Optical Engineering UCSC, Summer Ventures of Science and Math, 2001, 7 pp.)

There is therefore a need in the art for use in the biomedical analytical industries and the optical communications industries to provide more sensitive compositions and devices that are inexpensive to manufacture and easy to use.

BRIEF DESCRIPTION OF THE INVENTION

The present invention provides a chemical sensor comprising a plurality of particles, each particle comprising: a core, a shell having at least one surface and having contact with the core and wherein the shell comprises a sulfur-oxygen molecular species, and wherein the particle has been selectively sized using a notch filter and electromagnetic radiation, the electromagnetic radiation having a spectral wavelength of between about 350 nm and about 1075 nm. In one embodiment the particle has a size in the range of about 60 and 200 nm. In another embodiment the particle has a size selected from the range of between about 60 and 150 nm, between about 60 and 100 nm, between about 60 and 80 nm, between about 80 and 200 nm, between about 80 and 150 nm, between about 80 and 100 nm, between about 100 and 200 nm, between about 100 and 150 nm, and between about 150 and 200 nm.

In a preferred embodiment the core comprises a metal selected from the group consisting of gold, silver, platinum, copper, aluminum, palladium, cadmium, iridium, and rhodium. In a more preferred embodiment the core comprises gold.

In another preferred embodiment the electromagnetic radiation has a spectral wavelength of between about 350 nm and about 650 nm and between about 950 nm and about 1075 nm. In yet a more preferred embodiment the electromagnetic radiation has a spectral wavelength of between about 350 nm and about 775 nm and between about 875 nm and about 1075 nm.

In another embodiment, the chemical sensor comprises a shell that further comprises a linker molecule, the linker molecule selected from the group consisting of a thiol group, a sulfide group, a phosphate group, a sulfate group, a cyano group, a piperidine group, an Fmoc group, and a Boc group.

In yet a further embodiment, the chemical sensor comprises a support. In a preferred embodiment, the support comprises a medium that is permeable to an analyte of interest.

In another preferred embodiment, the chemical sensor has a surface wherein the surface can induce surface enhanced Raman scattering (SERS).

In still another preferred embodiment, the chemical sensor further comprises at least one detecting molecule, wherein the detecting molecule is bound to the surface. In a more preferred embodiment the detecting molecule is selected from the group consisting of proteins, peptides, antibodies, antigens, nucleic acids, peptide nucleic acids, sugars, lipids, glycophosphoinositols, and lipopolysaccharides.

In a yet more preferred embodiment the detecting molecule is an antibody. In another preferred embodiment, the detecting molecule is an antigen.

In another embodiment, the invention provides a chemical sensor further comprising at least one semiconductor quantum dot. In a preferred embodiment the semiconductor quantum dot further comprises a linker molecule, the linker molecule selected from the group consisting of a thiol group, a sulfide group, a phosphate group, a sulfate group, a cyano group, a piperidine group, an Fmoc group, and a Boc group.

In a still further embodiment, the invention provides a chemical sensor comprising at least one semiconductor quantum dot wherein the semiconductor quantum dot further comprises a detecting molecule, wherein the detecting molecule is bound to the semiconductor quantum dot. In a more preferred embodiment, the detecting molecule is selected from the group consisting of proteins, peptides, antibodies, antigens, nucleic acids, peptide nucleic acids, sugars, lipids, glycophosphoinositols, and lipopolysaccharides.

In a more preferred embodiment, the detecting molecule is an antibody. In the alternative, a more preferred embodiment comprises a chemical sensing device wherein the detecting molecule is an antigen.

Another embodiment of the invention provides a method for detecting an analyte in a sample using a chemical sensor, the method comprising the steps of: i) providing a sample; ii) providing a semiconductor quantum dot comprising a linker molecule (LM-SQD); iii) conjugating the analyte in the sample with the LM-SQD thereby producing an analyte-LM-SQD conjugate; iv) providing a chemical sensor comprising a plurality of particles, each particle comprising: a core, a shell having at least one surface and having contact with the core and wherein the shell comprises a sulfur-oxygen molecular species, and wherein the particle has been selectively sized using a notch filter and electromagnetic radiation, the electromagnetic radiation having a spectral wavelength of between about 350 nm and about 1075 nm, the shell surface further comprising a detecting molecule; v) incubating the analyte-LM-SQD conjugate with the chemical sensor for a predetermined time period; and vi) measuring the extent of binding between the analyte-LM-SQD conjugate and the chemical sensor; thereby detecting the analyte in the sample.

In a preferred embodiment the invention provides a method for detecting an analyte that is an ovarian cancer marker antibody. In one embodiment of the invention the detecting molecule in the chemical sensing device is an antigen that binds to an ovarian cancer marker antibody with an affinity ($K_a$) of at least $10^6$ l/mole. In a more preferred embodiment the $K_a$ is at least $10^8$ l/mole. In another preferred embodiment the analyte is a phospholipid. In a most preferred embodiment the phospholipid is lysophosphatidic acid (LPA).

In another embodiment, the invention provides an optical fiber, the fiber being shaped and adapted to provide a substrate surface for the chemical sensor. The fiber has a proximal end and a distal end. In one embodiment, the fiber is shaped having a D-shape cross-section; in another embodiment the distal end of the fiber is tapered to provide a large substrate surface. In a more preferred embodiment the fiber has at least two substrate surfaces.

In a yet additional embodiment, the invention provides an optical communications device comprising a fiber, a plurality of particles, each particle comprising: a core, a shell having at least one surface and having contact with the core and wherein the shell comprises a sulfur-oxygen molecular species, and wherein the particle has been selectively sized using a notch filter and electromagnetic radiation, the electromagnetic radiation having a spectral wavelength of between about 350 nm and about 1075 nm.

In a more preferred embodiment the optical communications device comprises a fiber, wherein the fiber is selected from the group consisting of ceramics, glasses, polymers, and metal-polymer composites. In one preferred embodiment the fiber cross-section is D-shaped. In another preferred embodiment the chemical sensor is disposed upon a surface of the fiber.

The invention also provides a method for synthesizing a chemical sensor comprising gold nanoparticle aggregates, the method comprising the steps of (i) providing one volume (1 V) of a solution of 0.1 M $HAuCl_4$; (ii) diluting the solution of $HAuCl_4$ with Milli-Q water to a final concentration of between $4\times10^{-4}$-$6\times10^{-4}$M $HAuCl_4$; (iii) combining the diluted solution of $HAuCl_4$ with a 0.1 M solution of $Na_2S$ to a final concentration of $HAuCl_4$ of between $4\times10^{-5}$-$6\times10^{-5}$ M $HAuCl_4$; (iv) incubating the combined solution for about between 60-120 minutes; and (v) measuring the extended plasmon band of the combined solution until the near-infrared (NIR) absorption is at a wavelength longer than 600 nm, thereby synthesizing a chemical sensing particle comprising gold nanoparticle aggregates. In one alternative, the 0.1 M solution of $Na_2S$ of step (iii) is substituted with an equal volume of 0.1M $Na_2S_2O_3$.

The invention also provides a method for coating gold nanoparticle aggregates onto a substrate, the method comprising the steps of (i) providing the gold nanoparticle aggregates as disclosed above; (ii) submerging the gold nanoparticle aggregates in a 5 mM aqueous solution of a tethering molecule, the tethering molecule selected from the group consisting of trimethoxy[3-(methylamino)propyl]silane (APS) and (3-mercaptopropyl)trimethoxy silane (MPS), a compound having a silane terminus and a thiol or amine terminus, and the like; (iii) incubating the gold nanoparticle aggregates with the tethering molecule to allow the gold nanoparticle aggregates to adsorb the tethering molecules; (iv) providing a substrate, wherein the substrate is selected from the group consisting of silicon dioxide, silicon, and the like; (v) sonicating the substrate in contact with a 2% solution of surfactant, the surfactant selected from the group consisting of HELLMANEX, ALCONOX, a small molecule alkaline surfactant, and the like; (vi) sonicating the substrate with 18 mΩ water; (vii) drying the substrate under nitrogen gas; (viii) depositing a volume of the adsorbed gold nanoparticle aggregates and tethering molecules solution onto the surface of the substrate; (ix) incubating the substrate with the solution for five seconds; (x) blowing the substrate dry with nitrogen gas; wherein the incubation time for step (iii) is selected from the group consisting of 30 minutes, 60 minutes, 90 minutes, and 120 minutes, the method resulting in gold nanoparticle aggregates coated onto a substrate.

The invention also provides a method for creating a chemical sensor with improved sensitivity, the method comprising the steps of: (i) providing the chemical sensing particle comprising gold nanoparticle aggregates as disclosed above; (ii) illuminating the gold nanoparticle aggregates with an amplified femtosecond beam at a flux of approximately 0.1 mJ/cm$^2$ for 1 hour; (iii) illuminating the gold nanoparticle aggregates using a tunable picosecond laser, thereby creating a chemical sensor with improved sensitivity.

BRIEF DESCRIPTION OF THE DRAWINGS

FIG. 7A is an illustration of an exemplary optical fiber having a substrate surface parallel to the axis of the fiber. FIG. 7B shows a cross-section of the distal section shown at the pair of arrows labeled '7B' on FIG. 7A.

FIG. 8A illustrates an alternative exemplary optical fiber having a single distal substrate surface at an angle to the axis of the fiber. FIGS. 8B, 8C, and 8D illustrate three cross-sections of the distal section at different positions along the length of the fiber shown at the pairs of arrows labeled '8B', 8C, and 8D, respectively, on FIG. 8A.

FIG. 9 illustrates the path of a photon within the fiber and shown interacting with a nanoparticle aggregate conjugated compound on the substrate surface of the fiber and the resulting SERS photon.

FIG. 10A illustrates another alternative exemplary optical fiber having two distal substrate surfaces. FIGS. 10B, 10C, and 10D illustrate three cross-sections of the distal section at different positions along the length of the fiber shown at the pairs of arrows labeled '10B', 10C, and 10D, respectively, on FIG. 10A.

FIG. 11 illustrates the path of photons within the fiber and shown interacting with nanoparticle aggregate conjugated compound on the substrate surfaces of the fiber and the resulting SERS photons.

FIG. 12 illustrates the distal end of a fiber positioned in proximity to the ends of two additional fibers that transmit the SERS photon to a detector.

FIG. 13 illustrates the angle of the distal substrate surface to the longitudinal plane of the fiber.

DETAILED DESCRIPTION OF THE INVENTION

The embodiments disclosed in this document are illustrative and exemplary and are not meant to limit the invention. Other embodiments can be utilized and structural changes can be made without departing from the scope of the claims of the present invention.

As used herein and in the appended claims, the singular forms "a," "an," and "the" include plural reference unless the context clearly dictates otherwise. Thus, for example, a reference to "a particle" includes a plurality of such particles, and a reference to "a surface" is a reference to one or more surfaces and equivalents thereof, and so forth.

1: Unique Properties of Novel Gold Nanoparticle Aggregates (GNA)

We have recently discovered that the reaction of chloroauric acid ($HAuCl_4$) with sodium sulfide ($Na_2S$) results in generation of novel gold nanoparticle aggregates (GNAs). These GNAs have unique optical and surface properties that are useful for applications, for example, surface enhanced Raman scattering (SERS), as a chemical sensor. SERS is a known and powerful technique for detecting molecules with high sensitivity and specificity. First, the GNAs we discovered are in aqueous solution and thereby naturally compatible with biological samples in water. Second, the GNAs have strong near IR absorption (650-1200 nm) that is ideal for biological applications due to better tissue penetration in this spectral region. Third, these GNAs have unique surface properties due to sulfur species on their surface that not only causes the aggregation in the first place but also provides a strong driving force for binding with chemical and biological molecules with high affinity for sulfur. Some of the potential applications will be outlined separately in the following sections.

The surface properties are undoubtedly due to the component sulfur and oxygen atoms (such as, but not limited to, molecules of negatively charged $S_xO_y$, wherein x=1 or 2 and y=1, 2, 3, or 4).

The particles can have a size range of about between 60 and 200 nm.

Figure 1:
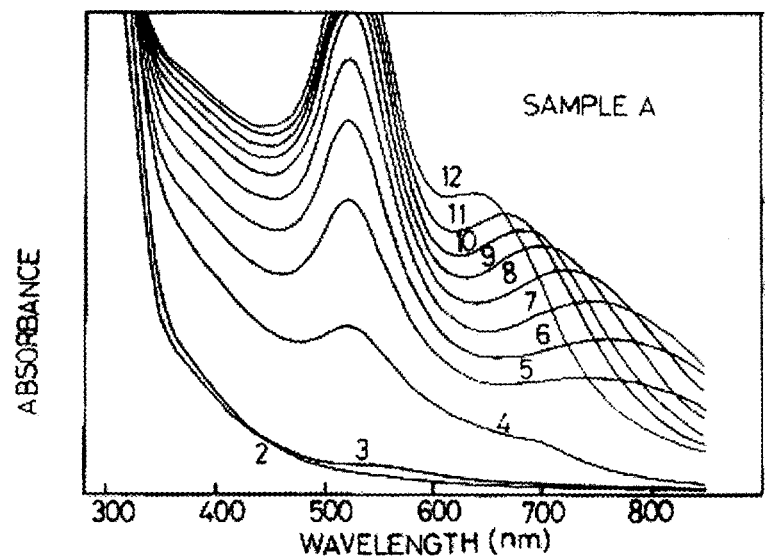
FIG. 1 shows representative electronic absorption spectra of gold nanoparticle aggregates in water during the growth and aggregation process.

FIG. 1 shows some representative electronic absorption spectra of the GNAs in water during the growth process. The spectrometer used limits the measurements to about 850 nm in the near IR. The strong near IR band is clearly visible in the spectra.

2. Optical Control and Manipulation of Distribution of Size/Shape of Gold Nanoparticle Aggregates and its Application for Optical Filters We have also discovered based on transient absorption and hole burning studies that the broad near IR absorption of the GNAs is inhomogeneously broadened due to a distribution of sizes and/or shapes (see FIG. 2). Since the hole burned is permanent, this immediately led us to propose the idea of using light (such as, but not limited to, high power lasers) to narrow the distributions of size/shape distribution. The idea is outlined in FIG. 3 using a combination of "white light" and notch filters to convert GNAs absorbing outside the notch filter covered region into GNAs that absorb only in the notch filter covered region. A significant increase in the number of GNAs in the notch filter covered region through this process is achieved.

This is useful since for many practical applications, for example, SERS and optical filters, it is highly desirable to narrow the distribution of size/shape of nanoparticle aggregates. For SERS in particular, the incident light has to be on resonance with the substrate absorption. Only those GNAs that have resonance absorption of the incident light are expected to be SERS active. It is thus extremely beneficial to have a narrow size/shape distribution and thereby narrow optical absorption.

A white light source with a particular wavelength blocked by an optical notch filter is used to irradiate a sample of GNA having a broad distribution of aggregate sizes and shapes. All the aggregates can be either destroyed and/or converted into the aggregates that absorb at the blocked wavelength. This can significantly reduce the size and shape distribution of the aggregates. Only aggregates that absorb (on resonance) with the blocked wavelength will remain and such aggregate samples are stable. This principle can work for many other metal nanoparticle aggregates such as silver, Pt, and Pd, etc. The size/shape-narrowed aggregates are useful for many applications such as SERS or can be used as an optical filter with a fairly narrow bandwidth. The aggregates can further be patterned onto a solid substrate and used for any application that can benefit from narrow distributed metal nanoparticle aggregates.

Figure 2:
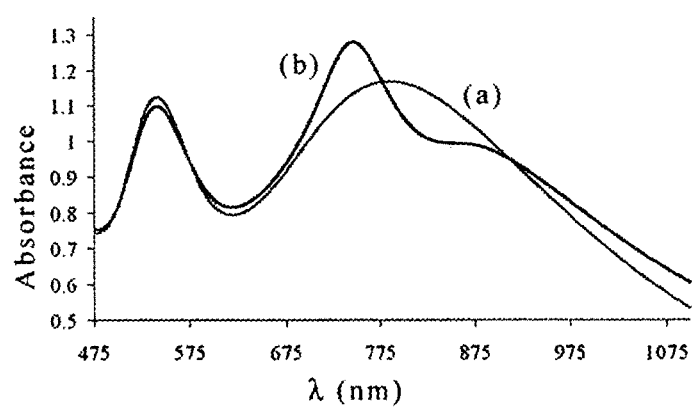
FIG. 2 shows results from a persistent spectral hole burning experiment using ~800 nm laser light at 200 μJ/pulse.
Figure 3:
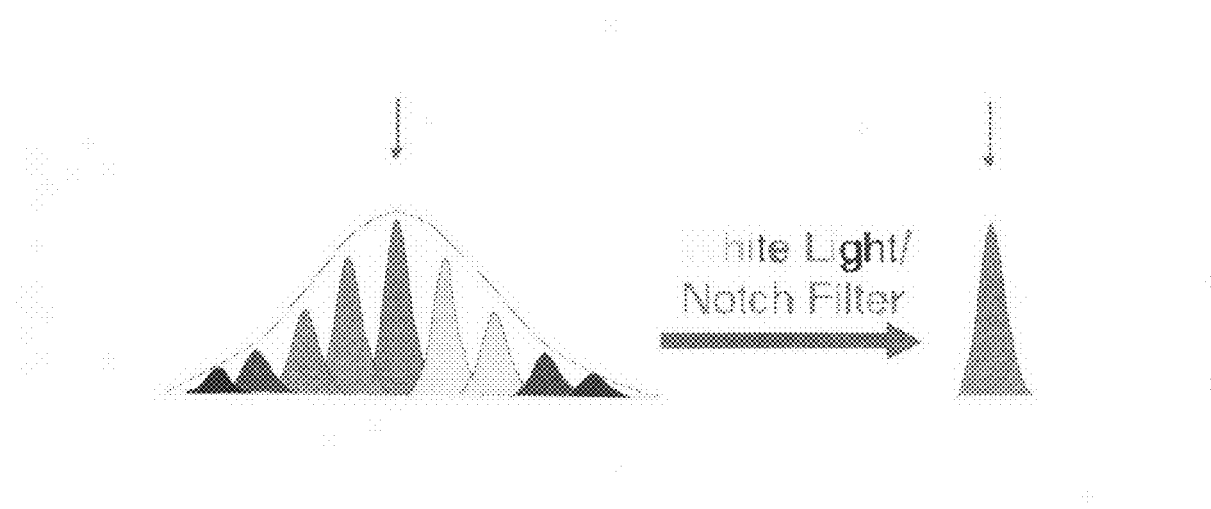
FIG. 3 shows an illustration of how narrowing aggregate size/shape distribution using light is achieved.

FIG. 2 shows the results of a persistent spectral hole burning experiment using ~800 nm laser light at 200 µJ/pulse. Trace a) is prior to laser irradiation. Trace b) is after 2.5 hours of hole burning. A hole is clearly seen in trace b) as well as a growth and shift of the maximum absorbance to bluer wavelengths. The SERS enhancement has been observed as being at about one-billion-fold ($10^9$) that is approximately three to four orders of magnitude greater than that disclosed in the prior art. Such an increase in enhancement therefore results in a reagent with greater sensitivity than other systems.

One potential application using this optical narrowing effect is proposed here. By exposing the aggregate solution to varying wavelengths of light it may be possible to burn away all but a narrow absorption band anywhere from 650 nm to 950 nm. This is shown schematically in the left portion of FIG. 3. As shown in the right portion of FIG. 3, a composition comprising particles having a narrow range of absorbance is created. By suspending these particles in glass, a low cost notch filter is produced. Current notch filters are highly expensive and difficult to produce. With this technology it is possible to produce good quality notch filters at very low costs. While these filters might not be as high quality as current high cost filters, there is a large market for low cost, low-end filters where high precision is not required. The market mainly comprises fiber-optical communications devices that are used to transmit information using photons instead of electrons. The devices comprise light amplifiers that retain the intensity of light as it travels through fiber optic networks. Light amplifiers are used to increase the intensity of weak light signals as they travel through long distances of fiber optic networks. The most commonly used form of light amplification is the Raman amplifier because it has proven to be the most efficient. This technique increases the frequency of transmitted light signals within a fiber optic network to prevent a loss of transferred data. This market has not currently been tapped in notch filters.

3. SERS Detection Applications for Sensing and Imaging

Raman spectroscopy is a powerful optical technique for detecting and analyzing molecules. Its principle is based on detecting light scattered off a molecule that is shifted in energy with respect to the incident light. The shift, called Raman shift, is characteristic of individual molecules, reflecting their vibrational frequencies that are like figure prints of molecules. As a result, the key advantage of Raman spectroscopy is its molecular specificity while its main limitation is the small signal due to low quantum yield of Raman scattering. One way to enhance the Raman signal is to tune the excitation wavelength to be on resonance with an electronic transition, so called resonance Raman scattering. This can usually produce an enhancement on the order of $10^2$-$10^3$. Another technique to enhance Raman scattering is surface enhancement by roughened metal surfaces, notably silver and gold, that provides an enhancement factor on the order of $10^6$-$10^8$. Similar or somewhat larger enhancement factors ($\sim 10^8$-$10^{10}$) have been observed for metal, mostly silver, nanoparticles.

In the last few years, it has been shown that an even larger enhancement ($\sim 10^{10}$-$10^{15}$) is possible for aggregates of metal nanoparticles, for example, comprising silver and/or gold. The largest enhancement factor of $10^{14}$-$10^{15}$ has been reported for rhodamine 6G (R6G) on single silver nanoparticle aggregates. This huge enhancement is thought to be mainly due to significant enhancement of the local electromagnetic fields of the nanoparticle aggregates that absorb strongly the incident excitation light for the Raman scattering process. With such large enhancement, many important molecules that are difficult to detect with Raman normally can now be easily detected. This provides many interesting and new opportunities for detecting and analyzing molecules using SERS with extremely high sensitivity and molecular specificity.

Of emphasis are the unique surface properties of the aggregates. It is these surface properties that make the gold nanoparticles aggregate in the first place and make the aggregates useful for SERS as a substrate with desirable properties.

Given the particular surface and optical features of the GNAs we have found, they can be suitable for SERS detection and analysis of a large number of molecules, including, but not limited to, proteins, DNA, explosives, chemical and biological warfare agents, toxins, and even virus and biological cells. We have demonstrated that the GNAs are SERS active for amino acids and DNA bases as well as antibodies for cancer detection. As discussed in Section 2 above, the possibility of narrowing the optical absorption of the GNAs for SERS is an important added advantage.

SERS can also be developed into a molecular imaging technique for biomedical and other applications. Exciting Raman imaging equipment may be usable for SERS imaging. SERS can provide an enhanced signal and thereby significantly shortened data acquisition time, making the technique practically useful for medical or other commercial and industrial applications including, but not limited to, chip inspection or chemical monitoring.

4. Antigen/Antibody Detection with Metal and Semiconducting Nanoparticles

Fluorescent nanoparticles (semiconductor quantum dots, SQDs) have been used recently as fluorescent biological markers and have been found to be extremely effective. They offer advantages including higher stability, stronger fluorescence, tunability of color, and possibility of optical encoding based on different sized or colored SQDs.

GNAs of the invention can be used to detect an analyte. Such an analyte can be, for example, but not limited to, an antigen, an antibody, a biochemical metabolite, an organic compound, a compound or element having biological activity, or the like.

Figure 4:
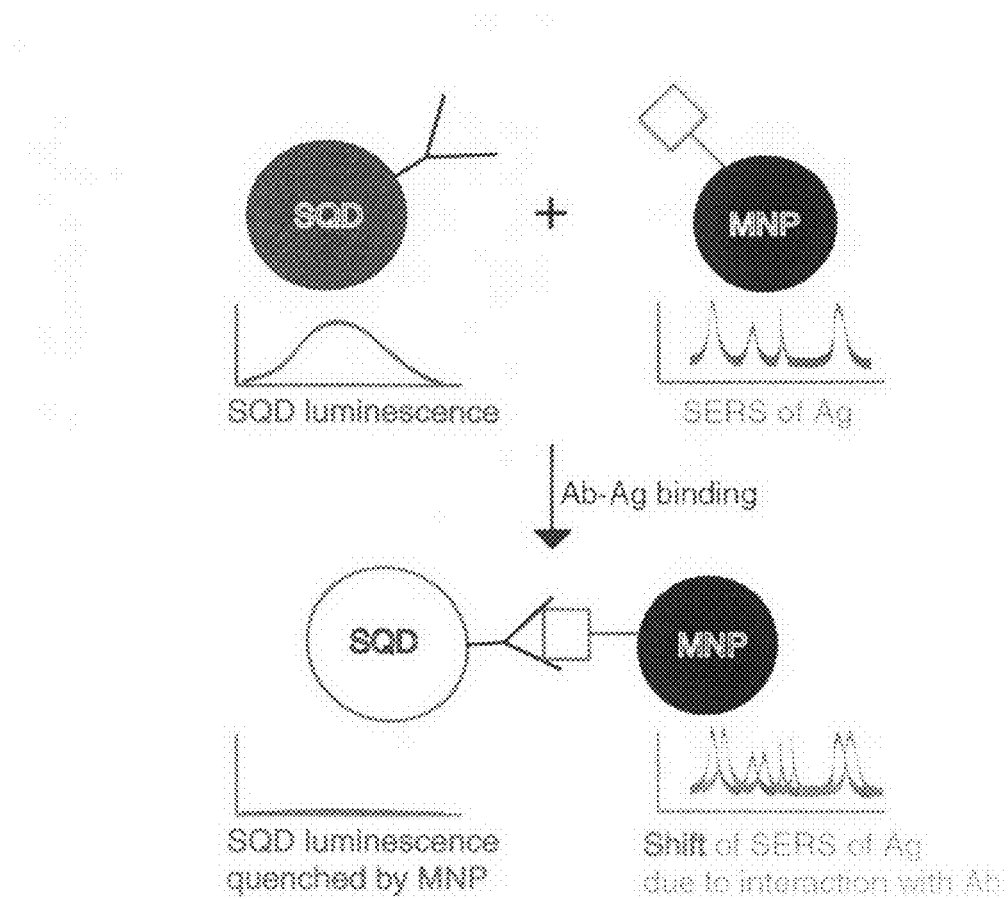
FIG. 4 shows a schematic illustration of how photoluminescence (PL) of an SQD-Ab conjugate is quenched by an MNP-Ag conjugate.

For example, the GNAs of the invention can be used in a novel dual optical scheme for sensitive and selective detection of antigens and is illustrated in FIG. 4. The technique is based on detection of photoluminescence from SQDs with antibody (Ab) attached and SERS (surface enhanced Raman scattering) spectra of antigen (Ag) attached to the GNAs that comprise metal nanoparticles (MNP). SERS spectrum is a measure of the Raman spectrum of the Ag that can be significantly enhanced by a metal nanoparticle. The Raman spectrum, similar to an infra-red (IR) spectrum, is characteristic of specific molecules due to the unique set of vibrational frequencies of each molecule. Before the Ag and Ab interact or bind to one another, we expect strong photoluminescence (PL) from the SQD and a well-defined SERS spectrum. Upon binding of Ab with the complementary Ag, two important consequences can occur. First, the PL from the SQD will be significantly, if not completely, quenched by the GNA-Ab complex. Second, the SERS spectrum of the Ag will change with small but noticeable frequency shift and/or relative spectral intensity changes due to Ag-Ab interaction. It is well known that PL from fluorophores can be significantly quenched when brought near a metal surface (bulk or nano-structured). The distance at which quenching occurs is a known parameter and is of the order of between about 1-2 nm for effective quenching. The distance will be dependent on the sizes of the SQD, GNA, Ag, and Ab, the length of a linker molecule (LM) between the SQD and the Ag (or alternatively, between the SQD and the Ab, between the GNA and Ab, or between the GNA and Ag), as well as on their relative binding configuration. We can estimate at this point that a certain favorable configuration and size will allow quenching. This is supported by a recent report from Wang et al. that PL quenching of a small, green-emitting QD with antibody attached by large, red-emitting QD with antigen attached occurs when the Ag and Ab interact (Wang et al. (2002) NanoLett., 2: 817-822). This experiment demonstrates that the distance can be close enough for effective PL quenching due to resonance energy transfer from the large QD to the smaller QD.

Figure 5:
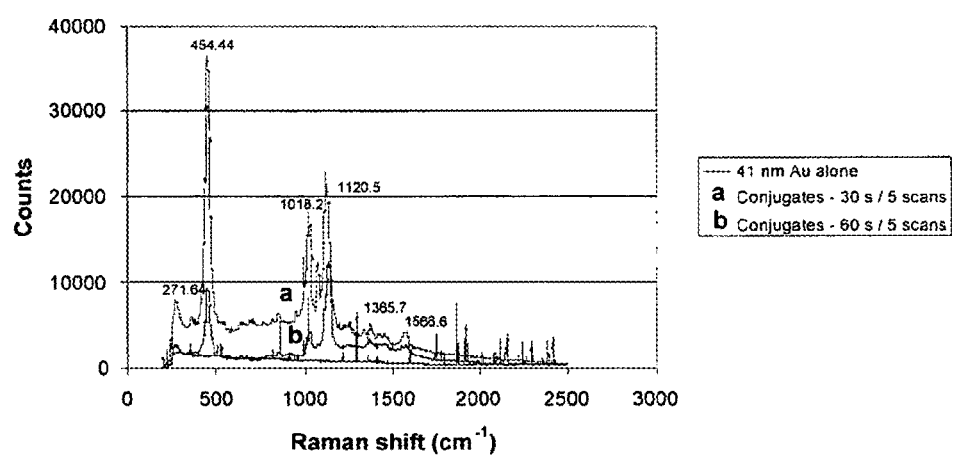
FIG. 5 shows the results of two SDQ quenching experiments: two SERS spectra of an SQD-Ab (polyclonal donkey anti-goat antibody) conjugate having been quenched by an MNP-Ag conjugate (pink and dark red) and one control SERS spectrum of an SQD without a conjugated Ab (blue).

As for the SERS aspect, we have very recently demonstrated that we can detect the SERS spectrum of a polyclonal Ab attached to gold nanoparticles through electrostatic interaction. FIG. 5 shows two representative SERS spectra where the reproducible peaks can be attributed to the Ab. To our best knowledge, this is the first demonstration of SERS detection of Ab. Since Raman or SERS spectrum is extremely sensitive to the structure, configuration and environment of a molecule, we anticipate that the SERS spectrum of an Ab can change upon interaction with its Ag.

The proposed scheme offers a novel technique for detecting antigen with high sensitivity (offered by both PL and SERS) and specificity (offered by both SERS and Ag-Ab interaction). In a typical experiment, we choose a laser wavelength that is on resonance with absorption of the QD (usually in the near UV and visible region) for measuring PL from the SQD with Ab attached, with and without binding to Ag attached to GNA. We then choose a laser wavelength that is off-resonance for the SQD absorption and produces no PL for SERS measurement (usually near IR) of the Ag attached to GNA, with and without binding with Ab attached to SQD. Comparing the two situations with and without Ag-Ab binding, we can see PL quenching of the SQD and SERS spectral change upon binding. Since the PL quenching of the SQD by a GNA is expected to be much more effective than a large SQD, the PL can be completely quenched in the situation with Ag-Ab binding. This is thus a zero-background experiment and can be much more sensitive than conventional PL detection that is typically not zero-background. For SERS, since the enhancement can be as high as $10^9$, it is almost as sensitive as fluorescence but has the extremely important advantage of direct molecular specificity between the Ag and the Ab.

In another example, the Ag can be replaced by a second Ab, the second Ab being specific for binding the first Ab. The second antibody can be from the same animal species as the first Ab, or can be from another animal species. Such first and second Abs are well known to those in the art and can be raised in and isolated from an animal such as, but not limited to, a rabbit, a human, a mouse, a rat, a monkey, an ape, a goat, a sheep, a cow, a pig, a donkey, a horse, a guinea pig, a whale, a wombat, a platypus, or the like.

SERS is also useful for detecting other cancer biomarkers that can interact or bind to the GNA surface. For example, Sutphen et al. have recently shown that lysophospholipids (LPL) are potential biomarkers of ovarian cancer (Sutphen et al. (2004) Cancer Epidemiol Biomarker Prev., 13: 1185-1191). Based on the molecular structure of LPL molecules, a favorable interaction between LPL molecules with GNA through electrostatic interaction can occur at the appropriate pH. In the case of the SERS experiment using a polyclonal Ab shown in FIG. 5, the strongest interaction with GNA occurs at the isoelectrostatic pH, i.e. pH at which the GNA has equal number of positive and negative charges. The pH is varied to adjust the charge on the GNA to determine the optimal pH or charge for strong interaction with LPL.

By conjugating fluorescent nanoparticle QDs to antigens and mixing the Ag-QD conjugate with a GNA-Ab composition, quenching of fluorescence upon binding of the antigen/antibody pair can be observed. The Ag and/or the Ab can be conjugated to the QD or GNA using a linker molecule (LM). A decrease in fluorescence can indicate the presence of the antibody for that particular antigen to which the fluorescing QDs have been attached. Depending on which antigen is utilized a wide array of antibodies can be detected. This can allow for the rapid detection of cancers or diseases that currently can take days or weeks to diagnose. Likewise, the scheme can work as well if antibody is attached to a fluorescent QD and the respective antigen to a metal nanoparticle. Metal particles have no florescence with visible excitation. The fluorescence quenching by metal nanoparticles can be more effective than quenching by larger QDs. This approach is sensitive and specific. The distance between the metal nanoparticle and QD is important for this to work (for example, the distance can be less than 2 nm). The interaction between the two components can be adjusted to achieve the maximum quenching effect.

5. Detection of Tumor Markers

Surface-enhanced Raman scattering using silver nanoparticles was applied to detect various forms of lysophosphatidic acid (LPA) to examine its potential application as an alternative to current detection methods of LPA as biomarkers of ovarian cancer. Enhancement of the Raman modes of the molecule, especially those related to the acyl chain within the 800-1300 $cm^{-1}$ region, was observed. In particular, the C—C vibration mode of the gauche-bonded chain around 1100 $cm^{-1}$ was enhanced to allow the discrimination of two similar LPA molecules. Given the molecular selectivity of this technique, the detection of LPA using SERS may eliminate the need for partial purification of samples prior to analysis in cancer screening.

Lysophosphatidic acid (LPA), originally known for its role as an intermediate in intracellular lipid metabolism, has now been recognized as an important multifunctional biological mediator that can elicit cellular responses including mitogenic and antimitogenic effects on the cell cycle, actin skeleton regulation, and cellular motility (see Tigyi et al. (1994) Proc. Nat. Acad. Sci. 91: 1908-1912; van Corven et al. (1989) Cell 59: 45-54; Ridley and Hall (1992) Cell 70: 389-399; and Zhou et al (1995) J. Biol. Chem. 270: 25549-25556). The involvement of LPA in inducing cell proliferation, migration and survival implicates it in the initiation and progression of malignant disease, and has been proposed as a sensitive biomarker for ovarian cancer (see Xu et al (1998) JAMA 280: 719-723; Mills and Moolenaar (2003) Nature Reviews 3: 582-591; Fang et al (2004) J. Biol. Chem. 279: 9653-9661; and Sutphen et al (2004) Cancer Epidemiol. Biomark. Prev. 13: 1185-1191).

Typically, the detection of LPA has been conducted using chromatography and mass spectroscopy assays that require a partial purification of the samples using thin layer chromatography (TLC) prior to analysis. Although this method is effective, an underestimation of LPA concentration can result during the recovery process due in part to the varying mobility of the LPA salts (free acid, sodium and calcium salts) when subjected to chromatography by TLC. The low stability of LPA also calls for fast and sensitive detection techniques.

A powerful optical detection technique based on surface-enhanced Raman scattering (SERS) offers a unique combination of high sensitivity and molecular specificity. With SERS, the Raman signal of a molecule is increased by many orders of magnitude as a result of strong enhancement of the excitation light through the resonance of the metal's surface electrons called the surface plasmon (see Moskovitz (1985) Rev. Modern Physics 57: 783-828; Otto et al. (1992) J. Phys. Condense Matter 4: 1143-1212; and Campion and Kambhampati (1998) Chem. Soc. Rev. 27: 241-250). SERS has been successfully used in the detection and analysis of a large number of chemicals and biological molecules (see Albrecht and Creighton (1977) J. Am. Chem. Soc. 99: 5215-5217; Nie and Emory (1997) Science 275: 1102-1106; Keating et al. (1998) J. Phys. Chem. B 102: 9414-9425; Kneipp et al (1998) Phys. Rev. E 57: R6281-R6284; and Schwartzberg et al. (2004) J. Phys. Chem. B 108: 19191-19197).

6. SERS Application for Detection and Analysis of Semiconductor Nanoparticles

Another application of SERS based on the gold nanoparticle system is for measuring Raman spectrum of semiconductor nanoparticles (QDs). Similar to molecules, normal Raman signals are very small and thus Raman spectrum is challenging to measure. SERS as an enhanced Raman technique for measuring Raman for semiconductor nanoparticles have not been reported before. The surface chemistry of the metal nanoparticles and the semiconductor QDs must be compatible for this to work. The sulfur species on the surface of the GNAs are ideal for II-VI SQDs to bind, enabling SERS detection of the SQDs. This provides a powerful method for detecting and analyzing semiconductor nanoparticles.

7. SERS for Raman Amplifier in Optical Communications

Figure 6:
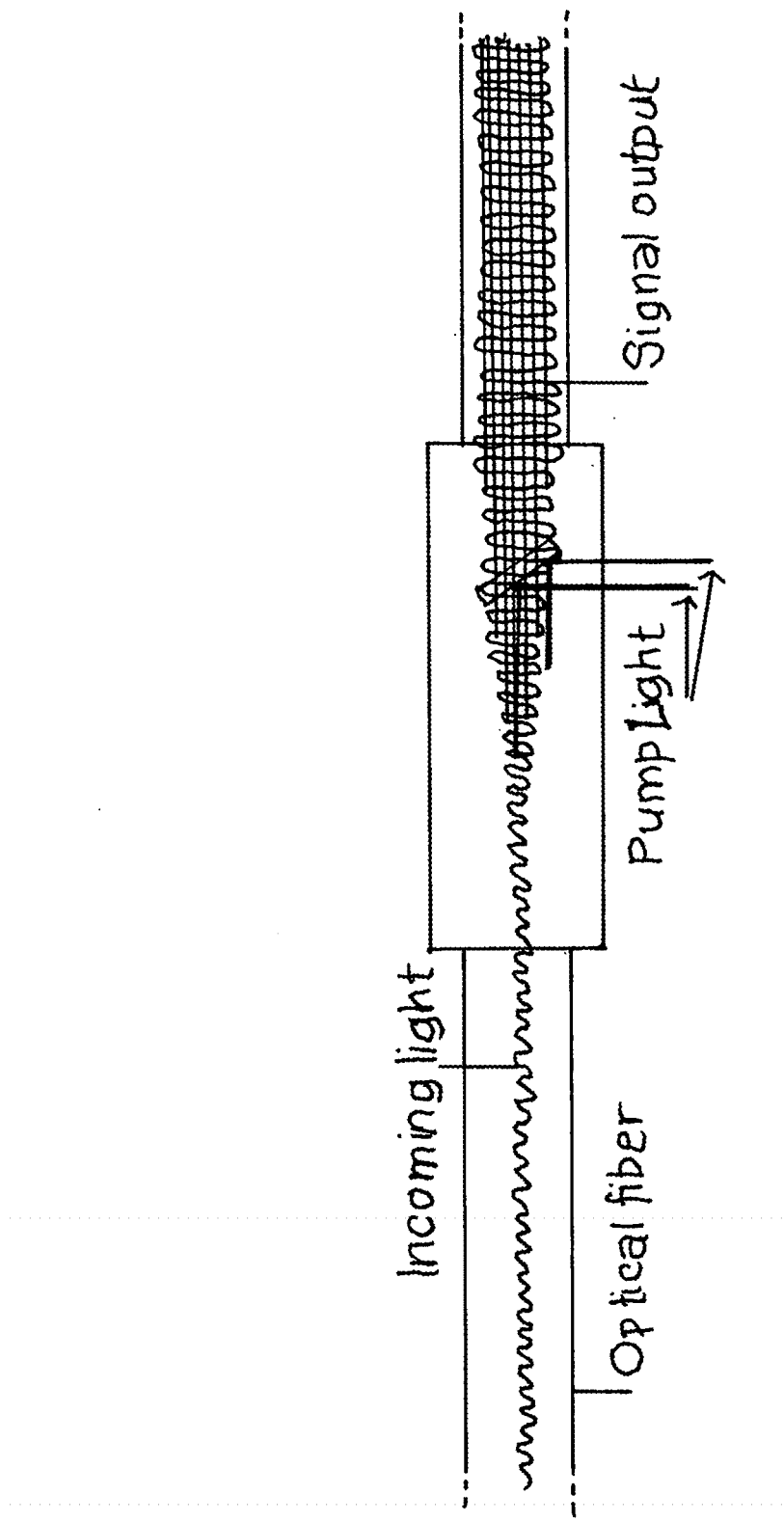
FIG. 6 is an illustration of how a Raman amplifier functions to intensify a photon beam.

Raman amplifiers have been used to amplify signal in optical communications (see, for example, FIG. 6). SERS can provide more amplification than normal Raman amplifiers. By doping MNPs, for example GNAs, into glass or polymer fibers, Raman scattering from the glass or polymer matrix can be used to amplify optical signal with the proper wavelength.

8. Synthesis of Biological Molecules

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker molecule. A linker molecule such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin.

Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full-length peptide is synthesized by sequential deprotection, coupling of derivatized amino acids, and washing with dichloromethane and/or N,N-dimethylformamide. The peptide is cleaved between the peptide carboxy terminus and the linker group to yield a peptide acid or amide. These processes are described in the Novabiochem 1997/98 Catalog and Peptide Synthesis Handbook (San Diego Calif. pp. S1-S20). Automated synthesis may also be carried out on machines such as the ABI 431 A peptide synthesizer (ABI). A protein or portion thereof may be purified by preparative high performance liquid chromatography and its composition confirmed by amino acid analysis or by sequencing (Creighton (1984) Proteins, Structures and Molecular Properties, WH Freeman, New York N.Y.).

In particular, a purified antigen may be used to produce antibodies or to screen libraries of pharmaceutical agents to identify those that specifically bind an antigen. Antibodies to an antigen may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with an antigen or with any fragment or oligopeptide thereof that has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface-active substances such as lysolecithin, pluronic polyols, polyanions, peptides, oil emulsions, keyhole limpet hemacyanin (KLH), and dinitrophenol. Among adjuvants used in humans, BCG (bacilli Calmette-Guerin) and *Corynebacterium parvum* are especially preferable. (For review of methods for antibody production and analysis, see, for example, Harlow and Lane (1988) Antibodies: A Laboratory Manual, Cold Spring Harbor Laboratory, Cold Spring Harbor, N.Y.)

It is preferred that the oligopeptides, peptides, or fragments used to induce antibodies to an antigen have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of antigen amino acids may be fused with those of another protein, such as KLH, and antibodies to the chimeric molecule may be produced.

Antibodies

Monoclonal antibodies to an antigen may be prepared using any technique that provides for the production of antibody molecules by continuous cell lines in culture. These include, but are not limited to, the hybridoma technique, the human B-cell hybridoma technique, and the EBV-hybridoma technique. (See, for example, Kohler et al. (1975) Nature 256: 495-497; Kozbor et al. (1985) J. Immunol. Methods 81: 31-42; Cote et al. (1983) Proc. Natl. Acad. Sci. 80: 2026-2030; and Cole et al. (1984) Mol. Cell Biol. 62: 109-120.)

In addition, techniques developed for the production of "chimeric antibodies," such as the splicing of mouse antibody genes to human antibody genes to obtain a molecule with appropriate antigen specificity and biological activity, can be used. (See, for example, Morrison et al. (1984) Proc. Natl. Acad. Sci. 81: 6851-6855; Neuberger et al. (1984) Nature 312: 604-608; and Takeda et al. (1985) Nature 314: 452-454.) Alternatively, techniques described for the production of single chain antibodies may be adapted, using methods known in the art, to produce antigen-specific single chain antibodies. Antibodies with related specificity, but of distinct idiotypic composition, may be generated by chain shuffling from random combinatorial immunoglobulin libraries. (See, for example, Burton (1991) Proc. Natl. Acad. Sci. 88: 10134-10137.)

Antibodies may also be produced by inducing in vivo production in the lymphocyte population or by screening immunoglobulin libraries or panels of highly specific binding reagents as disclosed in the literature. (See, for example, Orlandi et al. (1989) Proc. Natl. Acad. Sci. 86: 3833-3837; and Winter et al. (1991) Nature 349: 293-299.)

Antibody fragments that contain specific binding sites for an antigen may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, for example, Huse et al. (1989) Science 246: 1275-1281.)

Various immunoassays may be used for screening to identify antibodies having the desired specificity and minimal cross-reactivity. Numerous protocols for competitive binding or immunoradiometric assays using either polyclonal or monoclonal antibodies with established specificities are well known in the art. Such immunoassays typically involve the measurement of complex formation between an antigen and its specific antibody. A two-site, monoclonal-based immunoassay utilizing monoclonal antibodies reactive to two non-interfering antigen epitopes is preferred, but a competitive binding assay may also be employed. (Maddox, supra.)

Various methods such as Scatchard analysis in conjunction with radioimmunoassay techniques may be used to assess the affinity of antibodies for an antigen. Affinity is expressed as an association constant, $K_a$, which is defined as the molar concentration of antigen-antibody complex divided by the molar concentrations of free antigen and free antibody under equilibrium conditions. The $K_a$ determined for a preparation of polyclonal antibodies, which are heterogeneous in their affinities for multiple antigen epitopes, represents the average affinity, or avidity, of the antibodies for an antigen. The $K_a$ determined for a preparation of monoclonal antibodies, which are monospecific for a particular antigen epitope, represents a true measure of affinity. High-affinity antibody preparations with $K_a$ ranging from about $10^9$ to $10^{12}$ l/mole are preferred for use in immunoassays in which the antigen-antibody complex must withstand rigorous manipulations. Low-affinity antibody preparations with $K_a$ ranging from about $10^6$ to $10^7$ l/mole are preferred for use in immunopurification and similar procedures which ultimately require dissociation of antigen, preferably in active form, from the antibody. (See Catty (1988) Antibodies, Volume I: A Practical Approach, IRL Press, Washington, D.C.; and Liddell and Cryer (1991) A Practical Guide to Monoclonal Antibodies, John Wiley & Sons, New York, N.Y.)

The titre and avidity of polyclonal antibody preparations may be further evaluated to determine the quality and suitability of such preparations for certain downstream applications. For example, a polyclonal antibody preparation containing at least 1-2 mg specific antibody.ml$^{-1}$, preferably 5-10 mg specific antibody.ml$^{-1}$, is preferred for use in procedures requiring precipitation of antigen-antibody complexes. Procedures for evaluating antibody specificity, titer, and avidity, and guidelines for antibody quality and usage in various applications, are generally available. (See, for example, Catty, supra, and Coligan et al. supra.)

Preparation and Screening of Antibodies

Various hosts including, but not limited to, goats, rabbits, rats, mice, and human cell lines may be immunized by injection with antigen or any portion thereof. Adjuvants such as Freund's, mineral gels, and surface-active substances such as lysolecithin, pluronic polyols, polyanions, peptides, oil emulsions, KLH, and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique that provides for the production of antibodies by continuous cell lines in culture. These include, but are not limited to, the hybridoma technique, the human B-cell hybridoma technique, and the EBV-hybridoma technique. (See, for example, Kohler et al. (1975) Nature 256:495-497; Kozbor et al. (1985) J. Immunol. Methods 81:31-42; Cote et al. (1983) Proc. Natl. Acad. Sci. 80:2026-2030; and Cole et al. (1984) Mol. Cell. Biol. 62: 109-120.)

Alternatively, techniques described for antibody production may be adapted, using methods known in the art, to produce epitope-specific, single chain antibodies. Antibody fragments that contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab)2 fragments. Alternatively, Fab expression libraries may be constructed to allow rapid and easy identification of monoclonal Fab fragments with the desired specificity. (See, for example, Huse et al. (1989) Science 246: 1275-1281.)

The antigen, or a portion thereof, may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) Immunochemical Protocols, Humana Press, Totowa N.J.).

In the alternative, an antibody can be substituted by, for example, a chimeric protein that comprises a portion or fragment of a T-cell receptor (TCR). TCRs have an immunoglobulin domain that binds a cell-surface antigen comprising a host or a non-host molecule. Such molecules can be of viral origin or can be a particular cancer marker protein. The chimeric protein can also comprise a soluble protein (i.e. present in a bodily fluid or the cell cytoplasm) or a cell membrane-associated protein (such as a ligand receptor, an ion channel, or a molecule involved in signal transduction.

Metal nanoparticles are currently studied for a wide variety of biomedical applications including contrast imaging, ultrasonic imaging, thermal destruction of specific cancer cells, and laser tissue welding. All applications of this type rely on the optical and physical properties associated with metal nanoparticles, nominally of gold. Much of this work has focused on gold nanoshells due to their near IR optical absorption where tissue transmission is at its peak, making in-vivo applications feasible. This gold nanoparticle aggregate system possesses these same optical features with multiple advantages. While nanoshells can be tuned to absorb in a particular region, their absorption is inhomogenously broad and cannot be narrowed without significant purification. Therefore a significant percentage of nanoshells will be functionally useless at a given wavelength. Gold aggregates on the other hand can be tuned to have a very narrow absorption through the optical hole burning technique. With the absorption tuned to a given wavelength all aggregates will be utilized making them significantly more efficient for any of the above applications.

One of the most exciting of these applications is thermal destruction of cancer cells. The nanoparticle aggregates are selectively attached to cancer cells in a tumor by a passive mechanism that has been termed an "enhanced permeability and retention effect". The tumor mass is then illuminated with near IR laser light which passes harmlessly through the tissue, but is absorbed strongly by the aggregates, causing them to heat drastically, killing only the cancerous cells. (See O'Neal et al. (2004) Cancer Lett. 209: 171-176, herein incorporated by reference in its entirety.) This technology has been utilized with gold-silica nanoshells further comprising "stealthing" polymers, such as poly(ethyleneglycol) and derives thereof, or liposomes; however this can be done better with gold nanoparticle aggregates of the present invention.

9. Detection of Specific Compounds Using Optical Fibers

The nanoparticle aggregates can be used to detect specific compounds that may be at very low levels in a sample. Such a sample can be blood, urine, saliva, lung lavage, gastric fluid, lymphatic fluid, any other body fluid, or the like. In addition, the sample can be a sample of water or other aqueous medium, such as water from a spring, a stream, a river, a pond, a lake, a sea, or an ocean. The sample can be a geological sample such as from a geothermal spring, a lava evaporate or exudate, a hydrocarbon, or from an abyssal trench; a plant sample such as from the xylem or phloem of a stalk or trunk; a sample from a fluid in a man-made structure such as concrete, cement, aggregate, or the like; a sample of fluid from a piece of machinery such as an engine, motor, compressor, or the like.

The nanoparticle aggregates can be conjugated with antibody, the antibody having been synthesized to bind a specific compound. Such a specific compound can be a protein, a fatty acid, a carbohydrate, an organic compound based upon a benzene ring structure, an organic compound based upon a short chain hydrocarbon, a medium chain hydrocarbon or a long chain hydrocarbon. The specific compound can be modified with a reactive group. Such reactive groups are well known to those of skill in the art and can include phosphate groups, methyl groups, hydroxyl groups, sulphate groups, acetyl groups, or the like.

The nanoparticle aggregate-antibody conjugate complex has an altered SERS profile when the specific compound binds to the complex. The complex can be applied and incorporated onto a substrate surface of an optical fiber as disclosed herein. The exterior surface of the fiber comprises a compound that reflects photons. Such compounds are well known to those in the fiberoptic arts. The optical fiber has a proximal end or proximal section and a distal end or distal section. The distal end of a conventional fiber has a circular cross-section. A modified substrate surface can be created to create a substrate surface having an area larger than that of the distal end. The substrate surface of the fiber is created by removing a distal portion of the fiber section thereby creating a fiber with a distal end cross-section that is different from the distal end of the original fiber. The cross-section can be D-shaped, diamond-shaped, triangular, oval, or another non-symmetrical shape. Removing a portion of the fiber results in substrate surface with a larger surface area than the surface area of the original end of the fiber.

The resulting substrate surface can have a surface area that is up to at least about 8,000-fold larger than the distal end surface of the original fiber. The diameter of the fiber can be from between about 0.01 µm to about 10 µm. In one alternative, the diameter is from between about 0.1 µm to about 1 µm. In another alternative, the diameter is between about 0.2 µm to about 8 µm.

The complex is applied and incorporated onto the substrate surface and light is directed longitudinally through the fiber. The light can be coherent and/or non-coherent. The light interacts with the nanoparticle aggregate-antibody conjugate complex and a resulting SERS profile can be compared with a SERS profile from the nanoparticle aggregate-antibody conjugate complex that is bound with a known amount of specific compound. The SERS radiation is detected using a photon detector suitably disposed to detect the SERS radiation. The detector can be disposed at or near the substrate surface of the fiber at the distal end or distal section of the fiber, at or near the proximal end or proximal section of the fiber, or at another position as disclosed herein.

The fiber can have one or more such substrate surfaces. In the case of two substrate surfaces, the second substrate surface can reflect the SERS signal from the first substrate surface to the detector longitudinally along the length of the fiber, resulting in a markedly improved amplification of the SERS signal. Similarly, the first substrate surface can reflect a SERS signal from the second substrate surface to the detector.

In another alternative, at least one additional optical fiber can be positioned in proximity to the distal end or distal section of the fiber. The end of the additional fiber can have the same shape as the shape of the distal end or distal section of the fiber, such that SERS radiation emitted from the fiber is conducted through the additional fiber to a detector. Two additional fibers can be used in parallel where there are two new substrate surface s on the fiber.

The optical fiber can additionally have a non-uniform diameter, for example, the distal end having a cross-section perpendicular to the longitudinal plane that is larger in magnitude than a cross-section of the proximal end. Such a shape can further increase the amount of SERS radiation produced by a photon source.

The optical fiber can be made using glass, ceramics, or the like; or a polymeric compound such as cyclic olefin polymer (COP), polysulfone (for example, UDEL and RADEL resins), fluorinated terpolymers (such as those synthesized from tetrafluoroethylene, hexafluoropropylene, and vinylidene fluoride), polycarbonate, polyacrylate, polystryrene, or the like.

As illustrated in FIG. 13, the surface of the substrate surface (2) of the fiber (1) is at an angle θ (7) to the longitudinal plane (8) of the fiber. The angle θ is between 15° and 75°; preferably between 15° and 65°; more preferably between 15° and 45°; and most preferably between 15° and 35°. In one example, the angle 0 is 22.5°. The optimal preferable angle can be determined empirically to find the optimal angle for back-scattering of the SERS radiation.

One of skill in the art can readily determine which angle θ is optimal using data collected from experimentation as described above and knowledge of the composition of the fiber. It is well known in the art that different compositions have different refractive indices and one of skill in that art would know that different compositions will have a particular optimal refractive index. One of skill in the art would also know that it is not always necessary to create a fiber having a distal end section having a substrate surface at the optimal angle θ to the plane of the fiber since the nanoparticle aggregate-antibody conjugate complex can have different effects upon the refractivity of a fiber compound. It would require relatively little experimentation by one of skill in the art to determine the optimal preferable angle θ.

The SERS radiation can be further enhanced approximately 4-5-fold if an electrical field of a few Volts per centimeter (V/cm) is applied across the fiber, approximately perpendicular to the substrate surface. The potential difference can be maintained through an electrically conducting solution. The electrically conducting solution can be aqueous or non-aqueous but should not quench SERS radiation to the extent that the SERS enhancement due to the electrical field is quenched by the electrically conducting solution.

Examples of different optical fiber ends are illustrated in FIGS. 7 through 12. FIG. 7A illustrates a cylindrical fiber (1) having an exterior surface (3) and having a longitudinal portion removed from the distal section of the fiber thereby creating a substrate surface (2). FIG. 7B shows a cross-section of the distal section.

FIG. 8A illustrates an alternative distal section whereby a longitudinal portion is removed from the fiber at an included plane to the fiber resulting in a tapered distal end of the fiber. FIGS. 8B, 8C, and 8D illustrate three cross-sections of the distal section at different positions along the length of the fiber. FIG. 9 illustrates the path of a photon (4) from a photon source and the path of a SERS photon (5) from the substrate surface of the fiber to a detector (6).

FIG. 10A illustrates another alternative distal section whereby two longitudinal portions are removed from the fiber resulting in a tapered distal end of the fiber. FIGS. 10B, 10C, and 10D illustrate three cross-sections of the distal section at different positions along the length of the fiber. FIG. 11 illustrates the path of a photon (4) from the photon source and the path of a SERS photon (5) from the substrate surface (2) of the fiber to a detector (6).

FIG. 12 illustrates the distal end of a fiber positioned in proximity to the ends of two additional fibers that transmit the SERS photon to a detector. FIG. 13 illustrates the angle between the substrate surface (2) and the longitudinal plane (8) or axis of the fiber.

The nanoparticle aggregates can be formed and shaped into a desired shape, such as a sphere, a cylinder, a rod, a cone, a pyramid, or other shape, not limited to regular shapes, and deposited upon a substrate at a desired density using means well known to those of skill in the art. (See, for example, Fan et al. (2005) J. Vac. Sci. Technol. 8: 947-953; Chaney et al. (2005) Appl. Phys. Lett. 87: pub. no. 031908.)

EXAMPLES

The invention will be more readily understood by reference to the following examples, which are included merely for purposes of illustration of certain aspects and embodiments of the present invention and not as limitations.

Example I

Synthesis of Gold Nanoparticle Aggregates

The synthesis of the gold nanoparticle aggregates (GNAs) was performed as follows: 400-600 µl of a 0.02 M $HAuCl_4$ stock solution was diluted to $4\times10^{-4}$-$6\times10^{-4}$ M with Milli-Q water in glassware cleaned in aquaregia and rinsed with Milli-Q water to avoid contamination. To this, 40-60 µl of a 0.1 M solution of $Na_2S$ that has been aged for 2-3 months was added. After approximately 60-120 minutes, the color changed from a straw yellow to deep purple with the extended plasmon band (EPB) growing in between 600-1000 nm, indicating reaction completion. The aggregate formation was signified by strong near-infra-red (NIR) absorption at wavelengths longer than 600 nm. This reaction is also performed with sodium thiosulfate ($Na_2S_2O_3$) by replacing 1:1 the sodium sulfide solution, however, while these particles are optically identical to those that are sodium sulfide generated, they work poorly for SERS and should only be used for non detection applications. $HAuCl_4$, $Na_2S$, $Na_2S_2O_3$ and were obtained from Sigma-Aldrich (St. Louis Mo.) at the highest level of purity available.

Example II

Coating Gold Nanoparticle Aggregates onto Substrates/Fiber

The coating of gold nanoparticle aggregates onto a substrate/fiber was performed in two ways. First, by spin coating or drop casting a dilute solution of the aggregates onto the substrate. This yields a relatively thick film, however, it is not as stable as is necessary for many applications. The second method utilizes a tethering molecule, in this case trimethoxy [3-(methylamino)propyl]silane (APS). The substrate was cleaned prior to the silanization step by sonication in 2% solution of HELLMANEX or other surfactant, followed by 18 mΩ water.

The gold nanoparticle aggregates were then submerged in a 5 mM aqueous solution of APS to deposit the tethering molecules. After 1-2 minutes the substrate was rinsed with water, dried under nitrogen, and 40 W of the aggregate solution was placed on the surface. After several seconds exposed to the solution, it was blown dry with nitrogen. This provided a significantly thinner film than those made by spin or drop casting, however, it was extremely stable and robust under use. This film was made to near monolayer coverage by increasing the substrate exposure time to the APS and aggregate solutions to approximately 1 hour. APS was obtained from Sigma-Aldrich.

Example III

Band Narrowing in Gold Nanoparticle Aggregates

The extended plasmon band of the gold nanoparticle aggregates were tuned and narrowed via a regeneratively amplified, mode locked femtosecond Ti-sapphire laser system. This was done by illuminating the sample with the amplified femtosecond beam at a flux of approximately 0.1 $mJ/cm^2$. After approximately 1 hour, a deep, broad hole was burned in the absorption spectrum at near 800 nm while absorption to the blue drastically increased.

In order to tune the band to one particular wavelength a tunable picosecond laser is required. Due to the broad spectral linewidth of the femtosecond pulses it is impossible to completely narrow the extended plasmon band (EPB). By using the spectrally narrow picosecond pulses it is possible to selectively destroy the EPB to the blue and red of the desired excitation wavelength, enhancing the absorption more than two fold.

Example IV

Single Particle SERS/Luminescence and Bulk SERS

Samples for single particle experiments were prepared by immobilizing the GNAs or semiconductor quantum dots (SQD) on glass coverslips with trimethoxy[3-(methylamino)propyl]silane (APS). Coverslips were cleaned prior to the silanization step by sonication in 2% solution of Hellmanex, followed by 18 MΩ water. They were then submerged in 5 mM aqueous solution of APS to deposit the tethering molecules. After 1-2 minutes the coverslips were rinsed with water, dried under nitrogen, and 40 µl of the aggregate or SQD solution was placed on one surface. After several seconds exposed to the solution, it was blown dry with nitrogen.

Single particle experiments were performed on a custom designed confocal microscope built onto an inverted fluorescence microscope (Axiovert 100, Carl Zeiss, Inc., Thornwood N.Y.). A helium-neon or Argon ion laser depending on desired excitation wavelength was coupled into the back port of the microscope and directed into a high numerical aperture objective (Apochromat 100×, 1.4NA) that focused the light onto the sample surface. The sample was then raster scanned across the focused laser to generate an image using a commercially available piezoelectric scanner (Physik Instrumente, Auburn Mass.) and control electronics (Digital Instruments (Veeco Instruments Inc.) Woodbury N.Y.). The Raman scattered light or fluorescence was collected with the same objective used for excitation and focused onto a confocal aperture. The Rayleigh scattered light was then removed using a holographic notch filter (Kaiser Optical Systems, Inc., Ann Arbor Mich.) and the remaining scattered light was focused onto an avalanche photodiode (EG&G (CITY STATE)). Once a nanoparticle aggregate or QD was located, it was centered on the focused laser and the Raman scattering was directed into a spectrograph (Acton Instruments, Acton Mass.) that dispersed the light onto a liquid nitrogen cooled CCD camera (Princeton Instruments, Trenton N.J.). Typically six spectra (30 seconds each) were averaged. Bulk SERS experiments were performed on a Renishaw MICRORAMAN instrument (Renishaw Plc, Wotton-under-Edge, GL12 8JR, United Kingdom) with a 783 nm diode excitation laser. A drop of sample was placed on a quartz substrate and the laser was focused into the solution. Typically 4 spectra (30 seconds) were averaged.

Example V

Surface-Enhanced Raman Scattering Detection of Lysophosphatidic Acid

Lysophosphatidic acid (LPA), originally known for its role as an intermediate in intracellular lipid metabolism, has now been recognized as an important multifunctional biological mediator that can elicit cellular responses including mitogenic and antimitogenic effects on the cell cycle, actin skeleton regulation, and cellular motility. The involvement of LPA in inducing cell proliferation, migration and survival implicates it in the initiation and progression of malignant disease, and has been proposed as a sensitive biomarker for ovarian cancer.

Typically, the detection of LPA has been conducted using chromatography and mass spectroscopy assays that require a partial purification of the samples using thin layer chromatography (TLC) prior to analysis. Although this method is effective, an underestimation of LPA levels can result during the recovery process due in part to the varying mobility of the LPA salts (free acid, sodium and calcium salts) when subjected to chromatography by TLC. The low stability of LPA also calls for fast and sensitive detection techniques.

A powerful optical detection technique based on surface-enhanced Raman scattering (SERS) offers a unique combination of high sensitivity and molecular specificity. With SERS, the Raman signal of a molecule is increased by many orders of magnitude as a result of strong enhancement of the excitation light through the resonance of the metal's surface electrons called the surface plasmon. SERS has been successfully used in the detection and analysis of a large number of chemicals and biological molecules.

Here we report for the first time to our knowledge, the application of SERS using silver nanoparticles as a potential alternative technique for detecting LPA with high sensitivity and molecular specificity. Experimental results obtained for 16:0 LPA and 18:0 LPA successfully demonstrated not only that SERS of LPA can be measured but also that the SERS spectra of the two very similar LPA molecules were shifted enough in the 1100 $cm^{-1}$ region to uniquely identify them. The results suggested the strong potential for practical LPA detection using SERS-based techniques that are fast, sensitive, and molecular specific.

Powder samples of 16:0 LPA (1-Palmitoyl-2-hydroxy-sn-glycero-3-phosphate (sodium salt)) and 18:0 LPA (1-Stearoyl-2-hydroxy-sn-glycero-3-phosphate (sodium salt)) were purchased from Avanti Polar Lipids, Inc. Silver nitrate and sodium citrate were purchased from Sigma Aldrich (St Louis Mo.). Raman spectra were obtained using a Renishaw micro-Raman setup with a 50× objective lens and 780 nm excitation laser at 3 mW.

Silver nanoparticles were prepared using a synthesis from Lee and Meisel using silver nitrate as the metal precursor and a sodium citrate reducing agent (Lee and Meisel (1982) J. Phys. Chem. 86: 3391-3395). Formation of the silver nanoparticles was monitored using UV-visible spectroscopy using a HP 8452A spectrometer with 2 nm resolution. This nanoparticle solution was then concentrated by a factor of 10 via centrifugation prior to application. For the SERS experiment, 2 µl drops of the concentrated silver nanoparticles were placed on a glass slide and allowed to dry. Its Raman signal was obtained with one accumulation of a 30 second scan. After the silver had dried, 4 µl of a 100 µM solution of either the 16:0 LPA or 18:0 LPA (dissolved in Milli-Q water) was added on top of the silver to dry. The 4 µl volume ensured the complete coverage of the silver that had dried on the glass. The Raman signal was then collected using the same scan parameters. For comparison, Raman of the crystalline LPA samples was collected with five accumulations of a two-minute scan.

Figure 14:
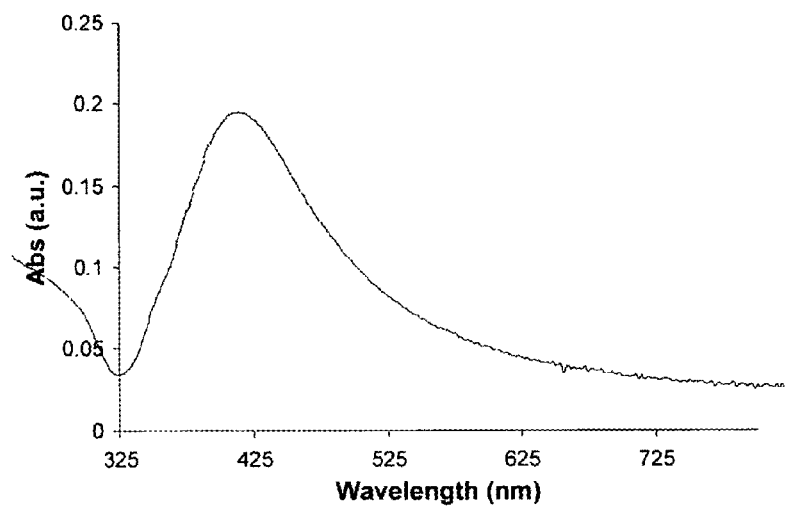
FIG. 14 shows a representative UV-visible absorption spectrum of silver nanoparticles. The absorption towards the 780 nm region is believed to be sufficient for SERS to occur.

The primary goal of this work was to demonstrate the ability of SERS to be selective, reproducible, and sensitive in detecting 16:0 LPA versus 18:0 LPA and show its potential as a viable alternative to current detection methods. FIG. 14 presents the UV-vis absorption spectrum of the silver nanoparticles used in this experiment. The surface plasmon band of these particles peaks near 400 nm, and contains very weak absorption around 780 nm, possibly due to some nanoparticle aggregation. For SERS to work effectively, resonance absorption of the metal nanoparticle substrate with the incident wavelength is essential (Schwartzberg et al. (2004) supra). The fact that there is only weak absorption near 780 nm while SERS has been demonstrated to work effectively suggests that either the weak absorption at 780 nm is enough for SERS occur, or the nanoparticles have further aggregated upon concentrating and drying for the SERS experiment that may have caused a red-shift of the absorption band and increased absorption at 780 nm similar to what has been observed for gold nanoparticles (Norman et al. (2002) J. Phys. Chem. B 106: 7005-7012).

Figure 15:
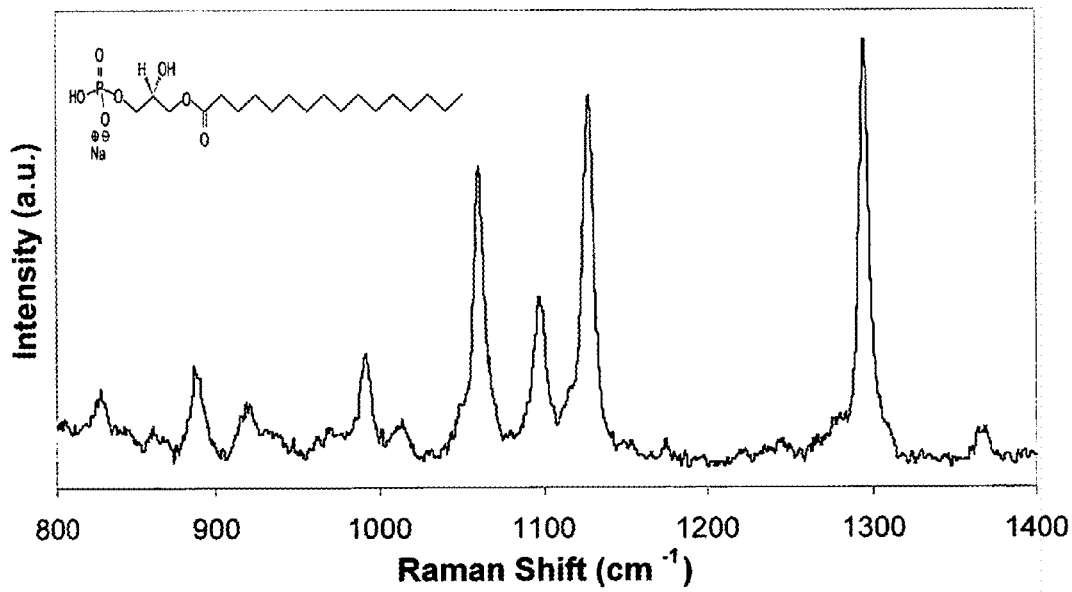
FIG. 15 shows a Raman spectrum of bulk lysophosphatidic acid crystals (780 nm excitation, 3 mW power) for 16:0 LPA.
Figure 16:
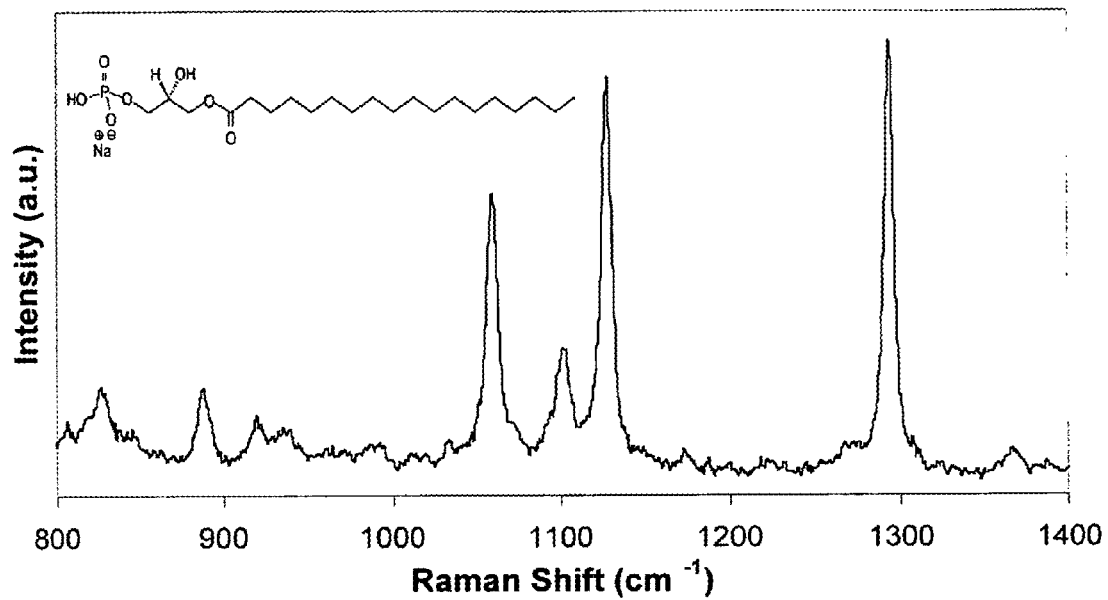
FIG. 16 shows a Raman spectrum of bulk lysophosphatidic acid crystals (780 nm excitation, 3 mW power) for 18:0 LPA.

The Raman spectra and molecular structures of the bulk crystal of 16:0 LPA and 18:0 LPA are presented in FIG. 15 and FIG. 16, respectively. With the only difference between the two LPAs being the length of their acyl chains, the ability to apply SERS for detection applications depends on its capacity to detect the acyl peaks. Hence, experimental measurements were performed between 800-1400 cm$^{-1}$ where many of the acyl peaks occur. The vibrational modes were assigned based on characteristic Raman frequencies (Lin-Vien et al. (1991) In: Infrared and Raman Characteristic Frequencies of Organic Molecules. Academic Press, Inc, San Diego Calif.). The band at 889 cm$^{-1}$ is representative of methylene rocking, and the 1294 cm$^{-1}$ band is typical of methylene twisting. The C—C skeletal stretching vibrations appeared between 1060 cm$^{-1}$-1130 cm$^{-1}$. In this region, information about the conformation of the carbon chain can also be obtained. The bands observed around 1060 cm$^{-1}$ and 1130 cm$^{-1}$ are characteristic of trans bonded carbon and the band observed around 1100 cm$^{-1}$ denotes the vibration of a gauche bonded chain. The analysis of the spectra obtained for these LPA samples compared well to Raman spectra of various lipids that have been previously analyzed (Dai et al (2005) Colloids and Surfaces B 42: 21-28; Krafft et al. (2005) Spectrochim. Acta (61): 1529-1535; Saint-Pierre Chazelet et al. (1994) Thin Solid Films 244: 852-856; and Suh (1992) Chem. Phys. Lett. 193: 327-330). Very strong similarities between the spectra of these two LPA molecules were noted, in particular the 889 cm$^{-1}$, 1294 cm$^{-1}$, 1060 cm$^{-1}$, and 1128 cm$^{-1}$ bands that they commonly share. Fortunately, the 16:0 LPA was distinguishable from the 18:0 LPA by the shift of the C—C vibration of the gauche-bonded chain from 1097 cm$^{-1}$ for 16:0 LPA to 1101 cm$^{-1}$ for 18:0 LPA.

Figure 17:
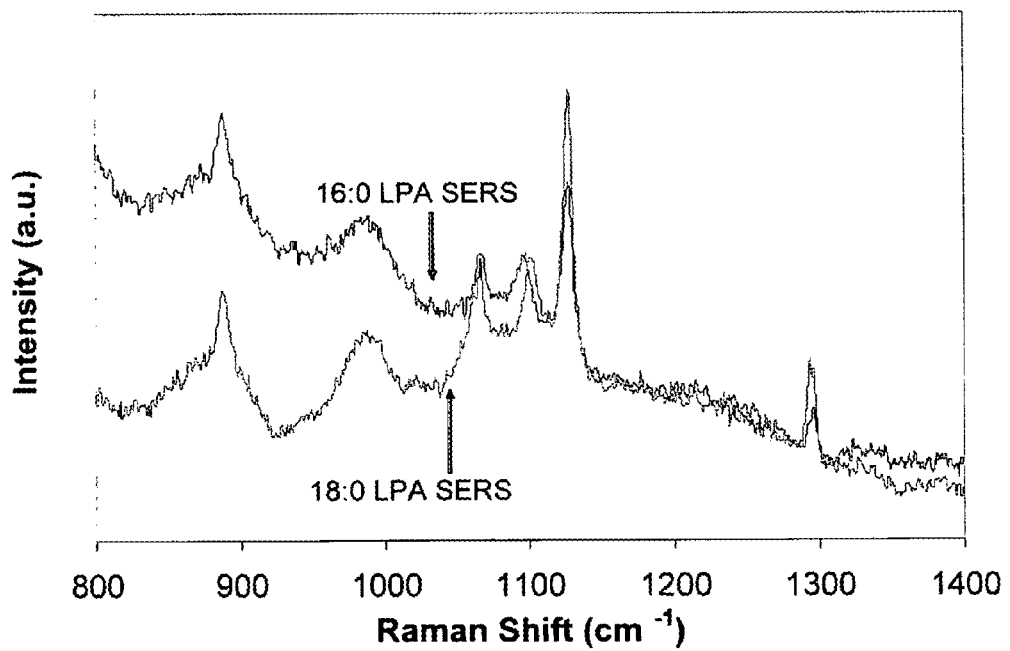
FIG. 17 shows SERS spectra of one hundred samples of $10^{-6}$ M solutions of 16:0 LPA and 18:0 LPA dried on silver nanoparticles (780 nm excitation, 3 mW power).
Figure 18:
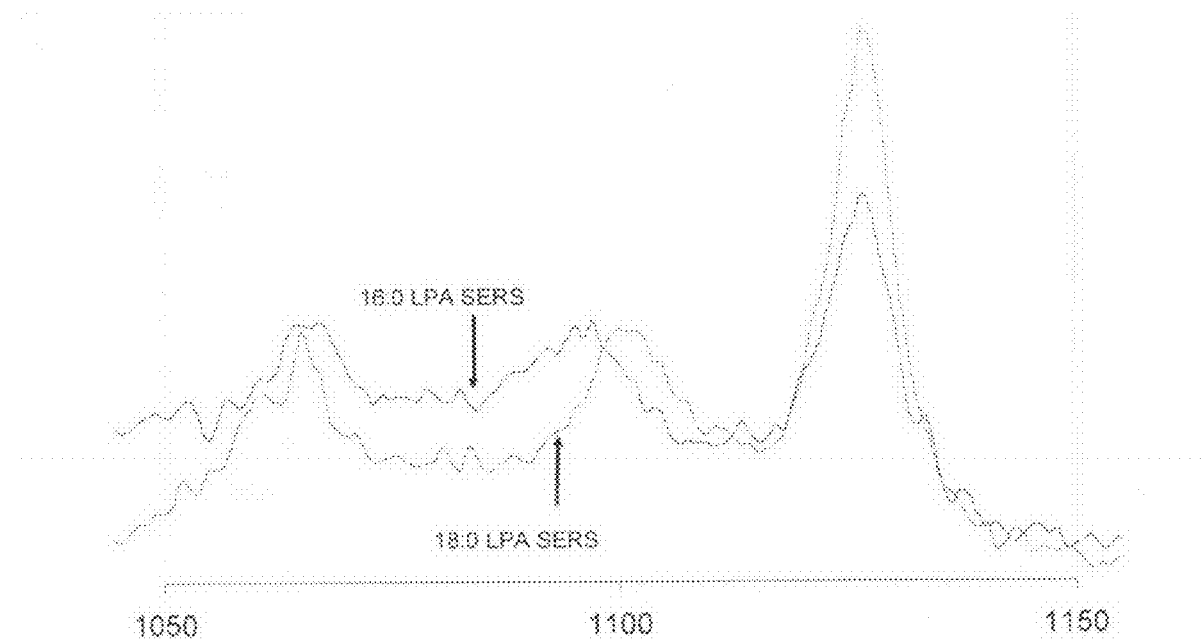
FIG. 18 shows the SERS region between 1050 $cm^{-1}$-1150 $cm^{-1}$ for 100×$10^{-6}$ M solutions of 16:0 LPA and 18:0 LPA to show the distinguishable mode at 1097 $cm^{-1}$ and 1101 $cm^{-1}$ (780 nm excitation, 3 mW power).

FIG. 17 presents the SERS spectra of the two LPA samples that were dried on the silver nanoparticles after subtracting the background signal of the dried nanoparticle solution. Attempts to obtain the Raman spectra of dried samples of LPA solutions without any silver present resulted in no signal, indicating that the presence of the silver enhanced the LPA Raman signal and made the detection of low concentrations possible. As expected, the bands of the acyl chain were enhanced using this technique with little to no shift from their bulk Raman positions. The SERS signal of the 16:0 LPA maintained its peaks of 889 cm$^{-1}$, 1097 cm$^{-1}$, 1128 cm$^{-1}$, and 1294 cm$^{-1}$, while 18:0 LPA maintained its peaks of 889 cm$^{-1}$, 1101 cm$^{-1}$, 1128 cm$^{-1}$, and 1294 cm$^{-1}$. FIG. 18 shows the region between 1050 cm$^{-1}$-1130 cm$^-$, demonstrating the ability of this procedure to detect the gauche peak that allows the acyl chains of the LPA samples to be distinguished from each other is clearly observed.

In SERS, the relative enhancement of a given mode implies the preferred orientation of the adsorbate to the surface of the metal. Typically, enhancement of a given mode is best when it is closest to the surface of the metal. Comparing the band intensities of the SERS spectrum of either LPA sample to its respective bulk spectrum shows that the two are quite similar (see Table 1). In other words, the intensity distribution of the SERS modes of 16:0 LPA exhibited a similar pattern of its bulk spectrum. The same pattern was observed for the 18:0 samples. This implied that no strong attraction was occurring between the nanoparticle surface and functional groups on the molecule to promote a specific orientation of the adsorbate. Also, with any strong surface interaction between the adsorbate and metal present, one would expect a shift in some bands of the SERS spectrum compared to the bulk Raman spectrum due to vibrational hindrance that would result from the adsorbate-metal surface interaction. This phenomenon was not observed in the LPA SERS spectra. The conclusion that no strong interaction was present between the metal surface and adsorbate could also be made from the fact that no immediate SERS was observed for mixed solutions of silver and LPA. The interaction between LPA and the nanoparticle surface was only strong enough for SERS to be observed when the molecule was dried on top of the silver.

TABLE 1

Comparison of the intensity of the assigned vibrational modes of the Raman spectrum of the bulk samples of LPA with its SER signal (W = weak, M = medium, S = strong, VS = very strong)

| Mode (cm$^{-1}$) | Assignment | 16:0 LPA | 16:0 SERS | 18:0 LPA | 18:0 SERS |
| --- | --- | --- | --- | --- | --- |
| 889 | CH$_2$ rock | M | M | M | M |
| 1060 | C-C vib (trans) | S | — | S | — |
| 1097 or 1101 | C-C vib (gauche) | M | M | M | M |
| 1128 | C-C vib (trans) | S | S | VS | VS |
| 1294 | CH$_2$ (twist) | S | W | VS | M |

Experiments to improve the sensitivity of this technique in terms of its ability to detect lower concentrations of various LPA in mixed samples along with actual samples of plasma/blood where other lysophospholipids besides LPA are present are performed. Some preliminary experiments using a prepared sample of mixed 16:0 and 18:0 LPA solutions had shown that this technique was able to distinguish the two different LPA molecules from each other in millimolar concentrations. However, in order to apply SERS for practical LPA detection, this technique should detect in micromolar quantities. As the surface interaction between the molecule and the nanoparticles play an important role in the effective enhancement of this technique, experiments are conducted with other metal nanoparticles capped with various surface agents that may induce stronger interactions between the acyl chain of the adsorbate and metal. We also can apply SERS detection of LPA using different shaped metal nanoparticles, as non-spherical particles with sharp edges or corners show stronger SERS activities than spherical particles (Schatz (1984) Acc. Chem. Res. 17: 370-376; Gersten (1980) J. Chem. Phys. 72: 5779-5780).

Example VI

Detection of Ab-GNP Binding Interaction Using a Secondary Ab

The effect of binding an antigen to its antibody is observed by taking the Raman spectrum of the antibody before and after exposure to the antigen through the use of SERS. To study the applicability of this method, a primary antibody (SC2020, Santa Cruz Biotechnology Santa Cruz Calif.) and a secondary antibody (SC1616, Santa Cruz Biotechnology Santa Cruz Calif.) were used. SC2020 was obtained at a concentration of 400 µg/ml and diluted by a factor of two with 20 mM HEPES buffer (pH 7.4). This solution was mixed equal volume with a GNP solution that was also diluted by a factor of two with 20 mM HEPES buffer. After twenty minutes of interaction, a SERS spectrum was obtained. An equal amount of SC1616 was added to the system and the SERS spectrum was obtained again. The binding of the secondary antibody (SC1616) to the primary antibody (SC2020) caused the SERS intensity of the secondary antibody to increase by 20-50%. This method provides an indirect means of detecting antigens in a system.

Example VII

Detection of Tumour-Antigens in Bodily Fluids

A murine monoclonal antibody raised against the CA125 ovarian cancer marker (OC125; Bast et al. (1981) J. Clin. Invest. 68: 1331-1337; Cat. No. AB19551, AbCam Ltd., Cambridge, UK) is incubated at a final concentration of 100 μg/ml in HEPES buffer (pH 7.4) with GNA as prepared above at a final concentration of 1 mg/ml for twenty minutes at ambient temperature. The mixture is then washed four times with excess sample buffer, then stored at 4° C. until use. A fraction is subjected to SERS to obtain baseline values.

Fluid samples from individuals with diagnosed ovarian cancer are incubated with SQD in the presence of a conjugating agent and linker molecule for 20 minutes at ambient temperature. The mixture is washed four times and resuspended in HEPES buffer (pH 7.4) to produce SQD-Ag conjugate. A fraction is subjected to SQD luminescence to obtain baseline values.

The SQD-Ag conjugate is added to OC125-GNA mixture in HEPES incubation medium (pH 7.4) at ambient temperature for 8 hours. Control samples are from individuals without diagnosed disease or disorders. The samples are then washed four times with incubation medium, resuspended in sample buffer, and then divided into two fractions. One fraction is subjected to SQD luminescence. The other fraction is subjected to SERS. Baseline values obtained earlier are then compared with the values obtained under experimental conditions.

Example VIII

Production of Antigen Specific Antibodies

Antigen substantially purified using polyacrylamide gel electrophoresis (PAGE; see, for example, Harrington (1990) Methods Enzymol. 182: 488-495) or other purification techniques is used to immunize rabbits and to produce antibodies using standard protocols. The antigen amino acid sequence is analyzed using DNASTAR software (DNASTAR Inc., Madison Wis.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, for example, Ausubel et al. supra, chapter 11.)

Typically, the oligopeptides are 15 residues in length, and are synthesized using an Applied Biosystems Peptide Synthesizer Model 431A using Fmoc-chemistry and coupled to KLH (Sigma-Aldrich, St. Louis, Mo.) by reaction with N-maleimidobenzoyl-N-hydroxysuccinimide ester to increase immunogenicity. (See, for example, Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG. In the alternative, a non-peptide antigen is used and is conjugated to KLH.

Example IX

Purification of Naturally Occurring Antigen Using Specific Antibodies

Naturally occurring or recombinant antigen is substantially purified by immunoaffinity chromatography using antibodies specific for the antigen. An immunoaffinity column is constructed by covalently coupling anti-antigen antibody to an activated chromatographic resin, such as CNBr-activated Sepharose (Pharmacia & Upjohn, Kalamazoo Mich.). After the coupling, the resin is blocked and washed according to the manufacturer's instructions.

Media containing antigen are passed over the immunoaffinity column, and the column is washed under conditions that allow the preferential absorbance of antigen (for example, high ionic strength buffers in the presence of detergent). The column is eluted under conditions that disrupt antibody/antigen binding (for example, a buffer of pH 2 to pH 3, or a high concentration of a chaotrope, such as urea or thiocyanate ion), and antigen is collected.

Example X

Identification of Molecules that Interact with Antigen

Antigen, or biologically active fragments thereof, are labeled with [$^{125}$I] Bolton-Hunter reagent. (See, for example, Bolton and Hunter (1973) Biochem. J. 133: 529-539.) Candidate molecules previously arrayed in the wells of a multi-well plate are incubated with the labeled antigen, washed, and any wells with labeled antigen complex are assayed. Data obtained using different concentrations of antigen are used to calculate values for the number, affinity, and association of antigen with the candidate molecules.

Example XI

SERS Sensor Based on D-Shaped Fiber

Fiber surface enhanced Raman scattering (SERS) sensors show great potential for in vivo and in vitro detection, however, current probes based on end polished fibers suffer from small signal due to their small active region. To overcome this, we propose and demonstrate a D-shaped fiber configuration to increase the detection area. Initial modeling has shown that most of the light can be absorbed by the SERS active layer coated on the polished fiber surface. Several orders of magnitude increase in surface area leads to substantially more detectable Raman scattered photons than those in end tip configurations. The SERS sensor based on D-shaped fibers has been demonstrated, for the first time, with excellent results using rhodamine 6G.

The majority of previous work in this area has utilized colloidal solutions or single use films to great effect, however, for practical applications the substrate must be portable, reusable, and robust (see Schwarzberg et al. (2004) supra; Tao et al. (2003) Nano Letters 3: 1229; van Duyne (2002) Abstracts of Papers of the American Chemical Society 223: 3; Sagmuller et al. (2003) J. Mol. Struct. 661: 279; Michaels et al. (2000) J. Phys. Chem. B 104: 11965; and Jana (2003) Analyst 128: 954). Recently, significant advancements have been made to this end. End tip fiber optic SERS probes have been shown to produce excellent results with high stability and portability, where a fiber with a flat, angled, or tapered tip was modified with silver island films, roughened silver films, or silver film over nanospheres to produce the SERS substrate (see Stokes et al. (2004) Applied Spectroscopy 58: 292; Stokes and Vo-Dinh (2000) Sensors and Actuators B-Chemical 69: 28; Mullen and Canon (1991) Anal. Chem. 63: 2196; Gessner et al. (2004) Analyst 129: 1193; Viets and Hill (1998) Sensors and Actuators B-Chemical 51: 92; Viets and Hill (2000) J. Raman Spectrosc. 31: 625; and Viets and Hill (2001) J. Mol. Struct. 565: 515). This configuration is highly advantageous, being reproducible, facile to fabricate, and inexpensive. The main limitation is the small number of SERS particles on the active fiber region, requiring high laser intensity and long integration times to attain reasonable SERS spectrum.

Figure 19:
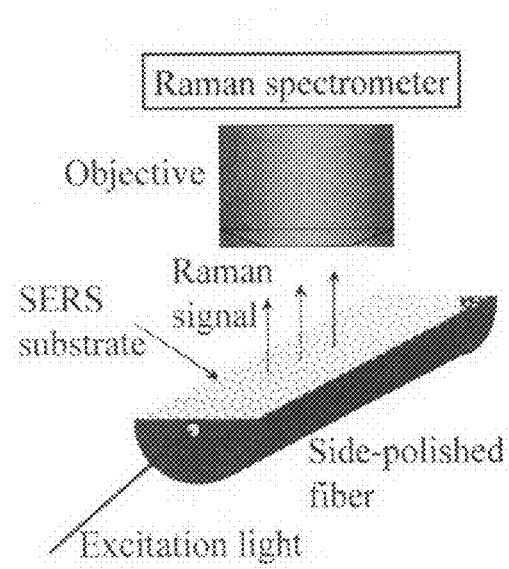
FIG. 19 illustrates a schematic of the Raman probe with a D-shaped (or side-polished) fiber coated with SERS substrate on the flat surface. Only the end segment of the fiber (about 1 cm) that is polished is shown. The rest of the unpolished fiber is about 0.5 m.

To overcome this hurdle, we chose to use a D-shaped fiber (DSF) configuration, so named because of the cross sectional D-shape formed by side polishing the fiber (see FIG. 19). Light can be coupled out of the polished fiber into silver or gold nanostructured films coated onto the polished surface, which can potentially increase the active surface area by several orders of magnitude. DSF has been used in a variety of applications including humidity, temperature, strain sensing, communication, optical switching, attenuators, and polarizers, but never for SERS detection, to our knowledge (see McCallion and M. Shimazu (1998) Laser Focus World 34: S19; Sohn et al. (2002) Sensors and Actuators A-Physical 101: 137; Alvarez-Herrero et al. (2000) IEEE Photonics Technol. Lett. 12: 1043; and Gu et al. (2003a) J. Optics A-Pure Appl. Optics 5: S420; Gu et al. (2003b), Optical Materials 23: 219).

Procedures for polishing the DSF have been described previously (Xu (2003) In-line fiber optical components for telecommunication in electrical engineering, University of California, Santa Cruz, Santa Cruz, Calif.). The surface of the flat polished plane was purposely left rough to facilitate nanoparticle binding and increase active surface area. Silver nanoparticles were synthesized by the method of Lee and Meisel (Lee and Meisel (1982) J. Phys. Chem. 86: 3391).

The SERS fibers were created by mixing 20 µl of silver nanoparticles with 5 µl of 0.1 mM rhodamine 6G (R6G) and drying a drop of this solution on the fiber under ambient conditions. SERS experiments were then performed on these devices in two configurations. A 780 nm diode laser is either coupled into the fiber (FIG. 19) or into a Renishaw micro-Raman spectrometer with a 20× objective. In both configurations the micro-Raman spectrometer collects the scattered light from the DSF. Samples were nominally integrated for 40 seconds for one scan with a laser intensity of ~3 mW.

On a highly polished DSF, little or no light would be coupled out of the fiber core. When the surface is roughened and coated with a layer of metal such as silver nanoparticles, light can be coupled into the coating layer to induce SERS. The amount of light coupled into the film is determined by several parameters including polishing depth, film thickness and density, and nature of the metal. The proper polishing depth should be determined by calculation, however, drop-casting a silver nanoparticle film onto the DSF ensures a thick coating which will couple the maximum amount of light from the fiber core into the SERS substrate.

Figure 20:
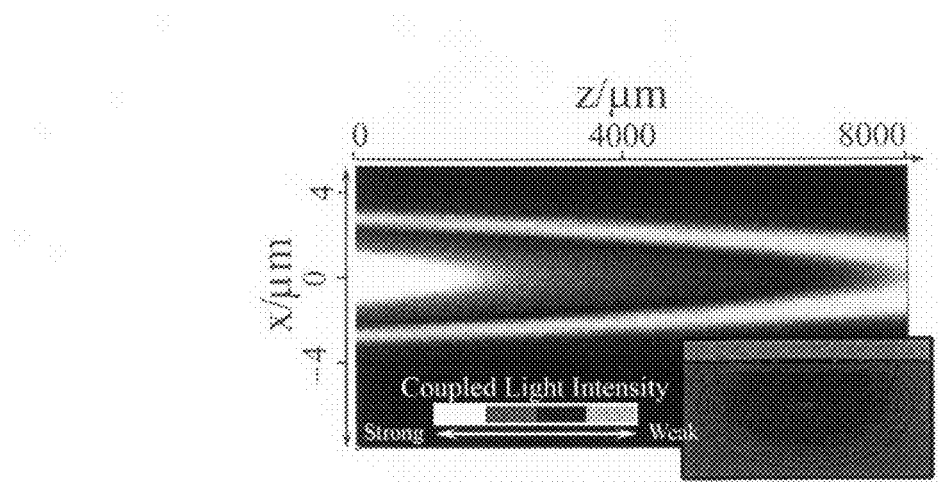
FIG. 20 illustrates the intensity distribution as light propagates through the D-shaped fiber covered with a silver film. Area shown is a cross-section parallel to the polished surface and through the center of the fiber core (top view). Inset: contour plot of the intensity distribution in a cross-section perpendicular to the fiber axis (end view). The semi-circle area is the fiber core with the cladding outside the half-circle. The thick black line above the semi-circle represents a 0.1 □m metal particle thin film and above the film (the top blue rectangle) is the air.

To determine how the light will be coupled out of the fiber into the SERS substrate, we simulated light propagation inside a D-shaped fiber covered with a solid silver film as the colloidal film, using FIMMWAVE software. Various film thickness, polishing depth, refractive index, and absorption constants were used in our simulation. We found that the amount of light being coupled into the metal layer strongly depends on the refractive index and the absorption constant of the metal. As an example, FIG. 20 shows the simulation result of a Corning 28e fiber covered with a silver nanoparticle aggregate layer. The plot in FIG. 20 shows the intensity distribution across the polished surface (top view illustrated). The fiber parameters were: core diameter 48 µm, $n_{core}$=1.450, cladding diameter 125 µm, $n_{clad}$=1.4447, and the polished surface cuts through the center of the fiber core. The metal film parameters were: thickness=0.1 µm, $n_{Ag}$=0.147, $\alpha_{Ag}$=82000/cm. Here a large absorption constant was chosen because of the resonant absorption of the Ag nanoparticle aggregates at 780 nm wavelength. With this choice of parameters, as light propagated through the side-polished section (from left to right in FIG. 20), the total intensity decreased due to coupling into the metal film and metal absorption, with only 30% remaining in the core at the end of the 1 cm side-polished fiber segment. The absorbed light activated SERS scattering over the entire 1 cm×8 µm=80,000 µm² surface region above the fiber core, as opposed to the 50 µm² of an end polished fiber of the same kind. As shown in the inset of FIG. 20, within a cross-section perpendicular to the fiber axis, light was mostly confined in the core region. Utilizing the DSF would increase the SERS active area, and consequently Raman scattered light, by as much as three orders of magnitude since light can be coupled into the metal layer over a substantial distance.

Figure 21:
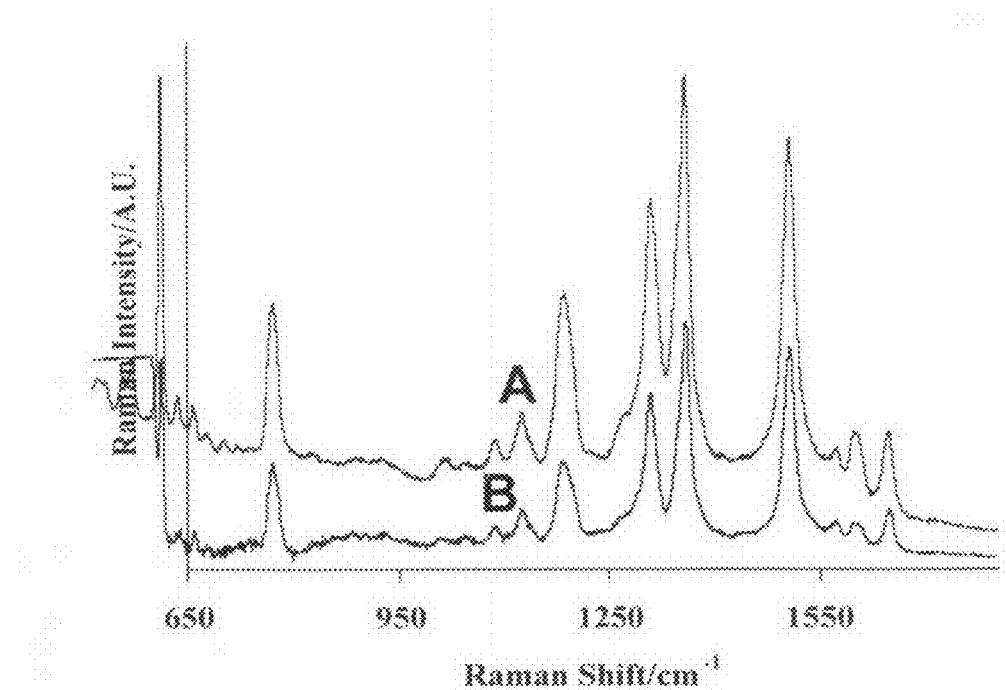
FIG. 21 illustrates a representative SERS spectra of rhodamine 6G on silver nanoparticles dried onto a D-shaped fiber collected with excitation laser incident to fiber surface (A) and coupled into the fiber (B).

Having confirmed the viability of the concept, SERS experiments were conducted using rhodamine 6G as a reference molecule resulting in excellent SERS data. With the laser coupled through the microscope and aligned perpendicular to the DSF surface, large enhancements are observed in the Raman modes of rhodamine 6G (FIG. 21, B). As expected, all peaks observed in the SERS spectrum were consistent with previous SERS results of rhodamine 6G (see Hildebrandt and Stockburger (1984) J. Phys. Chem. 88: 5935). More interestingly, instead of coupling light through the Raman optical microscope, light coupled into the fiber from the end of the fiber (see FIG. 19) produced similarly intense signals emitted and detected from the DSF surface (FIG. 21, A). In this case, light coupled from the core of the fiber into the silver nanoparticle film on the surface activates the plasmon mode and induced SERS of R6G on the film. It is important to note that after background subtraction the SERS spectra measured from both configurations were completely consistent. While peak intensities vary slightly, peak positions remained nearly constant. This indicated that the scattering mechanism was the same, independent of the excitation configuration.

One should be careful when comparing these spectra since their excitation intensities are different. The intensity of illumination through the microscope objective was high and confined to a small area due to the strong focusing of the excitation beam. The light coupled through the fiber had lower intensity over a larger area. Excitation intensity and surface area affect the scattering strength. The variations of peak intensities in the two spectra collected using two different illumination configurations could be partly due to the difference in excitation intensity.

In conclusion, we proposed and demonstrated a SERS sensor based on D-shaped fibers. Initial modeling had shown that as much as 70% of light coupled into the fiber may be absorbed into the SERS active layer across much of the 1 cm×8 µm surface, yielding an 80,000 µm² active region for a D-shaped fiber as compared to ~50 µm² of an end polished fiber of the same kind. This leads to as much as three orders of magnitude increase in Raman scattered photons compared to end tip fiber probes. The device was tested with rhodamine 6G with light directly illuminating the fiber surface and coupled through the fiber. Both configurations yield excellent and consistent SERS spectra of R6G. The experimental results, in conjunction with the theoretical modeling, demonstrated successfully that D-shaped fibers can serve as a convenient platform for SERS sensors that can potentially provide extremely high sensitivity and molecular specificity.

Those skilled in the art will appreciate that various adaptations and modifications of the just-described embodiments can be configured without departing from the scope and spirit of the invention. Other suitable techniques and methods known in the art can be applied in numerous specific modalities by one skilled in the art and in light of the description of the present invention described herein. Therefore, it is to be understood that the invention can be practiced other than as specifically described herein. The above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

We claim:

1. A method of forming a sensor, comprising the steps of:
   (A) providing an electromagnetic radiation source having a wavelength between 350 nm and 1075 nm;
   (B) providing a plurality of nanoparticle aggregates, wherein each of the nanoparticle aggregates comprise a diameter between 60 nm and 200 nm, a metallic molecular core, a sulfur-oxygen shell having a surface in contact with the core;
   (C) providing a notch filter, the notch filter having an electromagnetic wavelength absorption profile of between 650 nm and 950 nm;
   (D) selectively sizing by irradiating the plurality of nanoparticle aggregates provided in Step B with the electromagnetic radiation source of Step A through the notch filter provided in Step C and irradiating them with electromagnetic energy, the irradiating resulting in narrowing the optical absorption of the nanoparticle aggregates towards a selected surface plasmon resonance wavelength; the step resulting in selective-sized nanoparticle aggregates, and whereby the steps result in forming a sensor.

2. The method of claim 1 wherein the nanoparticle aggregates provided in step A have cores comprises a metal selected from the group consisting of gold, silver, platinum, copper, aluminum, palladium, cadmium, iridium, and rhodium.

3. The method of claim 1, the notch filter having an electromagnetic wavelength absorption profile of between 775 nm and 875 nm.

4. The method of claim 1 wherein the plurality of nanoparticle aggregates provided in step B have shells comprising a linker molecule selected from the group consisting of a thiol group, a sulphide group, a phosphate group, a sulphate group, a cyano group, a piperidine group, an Fmoc group, and a Boc group.

5. The method of claim 1 wherein the selective sizing performed in step D is performed by irradiating the nanoparticle aggregates provided in step B with a laser beam.

6. The method of claim 1, wherein the selected surface plasmon resonance in step D is surface enhanced Raman resonance.

7. The method of claim 6, wherein the sensor is a surface enhanced Raman sensor.

8. The method of claim 7, wherein step D includes inducing surface enhanced Raman scattering.

9. The method of claim 6, wherein the surface enhanced Raman scattering is used for detecting a molecule.

10. The method of claim 9 wherein the molecule for detecting is selected from the group consisting of proteins, peptides, antibodies, antigens, nucleic acids, peptide nucleic acids, sugars, lipids, glycophosphoinositols, and lipopolysaccharides.

11. The method of claim 1, further including a step E of supporting the nanoparticle aggregates selectively sized in step D.

12. The method of claim 11, wherein step E includes providing a support permeable to an analyte of interest.

13. The method of claim 1, wherein the plurality of nanoparticle aggregates provided in step B have shells comprising a linker molecule semiconductor quantum dot.

14. The method of claim 13 wherein the plurality of nanoparticle aggregates provided in step B includes a detecting molecule bound to the semiconductor quantum dot.

15. The method of claim 14 wherein the detecting molecule is selected from the group consisting of proteins, peptides, antibodies, antigens, nucleic acids, peptide nucleic acids, sugars, lipids, glycophosphoinositols, and lipopolysaccharides.

16. The chemical sensor of claim 14 wherein the detecting molecule is an antigen that binds to an ovarian cancer marker antibody with an affinity ($K_a$) of at least $10^6$ l/mole.

* * * * *